(12) United States Patent
Maetzke et al.

(10) Patent No.: US 6,552,187 B1
(45) Date of Patent: Apr. 22, 2003

(54) PROCESS FOR THE PREPARATION OF HERBICIDAL DERIVATIVES

(75) Inventors: Thomas Maetzke, Münchenstein (CH); René Mutti, Basel (CH); Henry Szczepanski, Wallbach (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/980,240
(22) PCT Filed: Jun. 14, 2000
(86) PCT No.: PCT/EP00/05476
§ 371 (c)(1), (2), (4) Date: Nov. 29, 2001
(87) PCT Pub. No.: WO00/78881
PCT Pub. Date: Dec. 28, 2000

(51) Int. Cl.$^7$ .............................................. C07D 498/02
(52) U.S. Cl. ...................... 540/545; 540/469; 544/66; 548/126; 548/143
(58) Field of Search ................................ 540/469, 545; 544/66; 548/126, 143

(56) References Cited

U.S. PATENT DOCUMENTS 5,358,924 A  10/1994 Kruger et al.
6,410,480 B1 * 6/2002 Muhlebach et al. ........ 504/105

FOREIGN PATENT DOCUMENTS

WO   WO 99/47525   9/1999

OTHER PUBLICATIONS

Woodman and Stonebraker, Tetrahedron Lett., vol. 51, 1970, pp. 4473–4476.
Zvilichovsky et al., J. Org. Chem., vol. 60, No. 16, 1995, pp. 5250–5254.
Voghel et al., J. Org. Chem., vol. 39, No. 9, 1974, 1233–1235.
Bedereck et al., Chem. Berichte, vol. 103, No. 1, 1970, pp. 210–221.
Buyle et al., Tetrahedron, vol. 25, No. 16, pp. 3447–3451, 1969.

* cited by examiner

Primary Examiner—Joseph K. McKane
Assistant Examiner—Rebecca Anderson
(74) Attorney, Agent, or Firm—William A. Teoli, Jr.; Rose M. Allen

(57) ABSTRACT

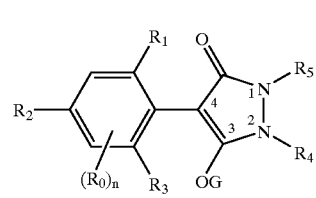
(I)

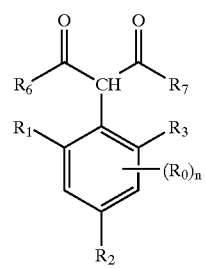

(II)

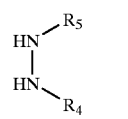

(IV)

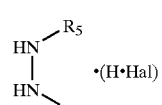

(IVa)

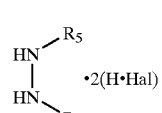

(IVb)

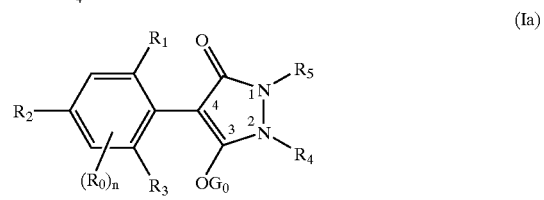

(Ia)

A process for the preparation of compounds of formula (I), which process comprises reacting a compound of formula (II), in an inert organic solvent, optionally in the presence of a base, with a compound of formula (IV), (IVa) or (IVb), and optionally converting the resulting compound of formula (I) wherein G is a metal ion equivalent or an ammonium cation, by salt conversion into the corresponding salt of formula (I) wherein G is a sulfonium or phosphonium cation, or by treatment with a Brönsted acid into the corresponding compound of formula (I) wherein G is hydrogen, and 'in situ' conversion of compounds of formula (I) with an electrophile of formula (XII) or (XIId) $G_0$—L (XII) or $R_{32}$—N=C=$X_3$ (XIId), optionally in the presence of an acid-binding agent or a catalyst, to the compounds of formula (Ia).

12 Claims, No Drawings

PROCESS FOR THE PREPARATION OF HERBICIDAL DERIVATIVES

This is a 371 of international application PCT/EP00/05476 with international filing date Jun. 14, 2000.

The present invention relates to a new process for the preparation of herbicidally active substituted 3-hydroxy-4-aryl-5-oxopyrazoline derivatives.

3-Hydroxy-4-aryl-5-oxopyrazolines having herbicidal action and the preparation thereof are described, for example, in WO 92/16510, EP-A-0 508 126, WO 95/01971, WO 96/21652, WO 96/25395, WO 97/02243 and in WO 99/47525.

Surprisingly, it has now been found that substituted 3-hydroxy-4-aryl-5-oxopyrazoline derivatives can readily be prepared in a high yield and with a high degree of purity by the condensation of arylmalonic acid diamides or arylmalonic acid monoamides with hydrazine derivatives.

The present invention accordingly relates to a process for the preparation of compounds of formula I:

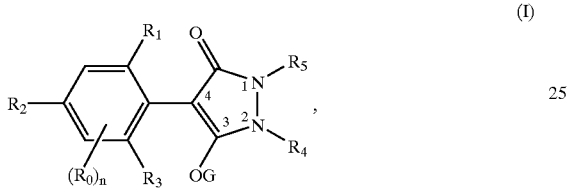

(I)

wherein $R_0$ is, each independently of any other, halogen, $C_1$–$C_6$alkyl, $C_2$–$C_6$alkenyl, $C_2$–$C_6$alkynyl, $C_1$–$C_6$haloalkyl, cyano-$C_1$–$C_6$alkyl, $C_2$–$C_6$haloalkenyl, cyano-$C_2$–$C_6$alkenyl, $C_2$–$C_6$haloalkynyl, cyano-$C_2$–$C_6$alkynyl, hydroxy, hydroxy-$C_1$–$C_6$alkyl, $C_1$–$C_6$alkoxy, nitro, amino, $C_1$–$C_6$alkylamino, di($C_1$–$C_6$alkyl)amino, $C_1$–$C_6$alkylcarbonylamino, $C_1$–$C_6$alkylsulfonylamino, $C_1$–$C_6$alkylaminosulfonyl, $C_1$–$C_6$alkylcarbonyl, $C_1$–$C_6$alkylcarbonyl-$C_1$–$C_6$alkyl, $C_1$–$C_6$alkoxycarbonyl-$C_1$–$C_6$alkyl, $C_1$–$C_6$alkylcarbonyl-$C_2$–$C_6$alkenyl, $C_1$–$C_6$alkoxycarbonyl-$C_2$–$C_6$alkenyl, $C_1$–$C_6$alkylcarbonyl-$C_2$–$C_6$alkynyl, $C_1$–$C_6$alkoxycarbonyl-$C_2$–$C_6$alkynyl, $C_1$–$C_6$alkoxycarbonyl, cyano, carboxyl, phenyl or an aromatic ring that contains 1 or 2 hetero atoms selected from the group consisting of nitrogen, oxygen and sulfur, wherein the latter two aromatic rings may be substituted by $C_1$–$C_3$alkyl, $C_1$–$C_3$haloalkyl, $C_1$–$C_3$alkoxy, $C_1$–$C_3$haloalkoxy, halogen, cyano or by nitro; or $R_0$, together with the adjacent substituents $R_1$, $R_2$ and $R_3$, forms a saturated or unsaturated $C_3$–$C_6$hydrocarbon bridge that may be interrupted by 1 or 2 hetero atoms selected from the group consisting of nitrogen, oxygen and sulfur and/or may be substituted by $C_1$–$C_4$alkyl;

$R_1$, $R_2$ and $R_3$ are each independently of the others hydrogen, halogen, $C_1$–$C_6$alkyl, $C_2$–$C_6$alkenyl, $C_2$–$C_6$alkynyl, $C_3$–$C_6$cycloalkyl, $C_1$–$C_6$haloalkyl, $C_2$–$C_6$haloalkenyl, $C_1$–$C_6$alkoxycarbonyl-$C_2$–$C_6$alkenyl, $C_1$–$C_6$alkylcarbonyl-$C_2$–$C_6$alkenyl, cyano-$C_2$–$C_6$alkenyl, nitro-$C_2$–$C_6$alkenyl, $C_2$–$C_6$haloalkynyl, $C_1$–$C_6$alkoxycarbonyl-$C_2$–$C_6$alkynyl, $C_1$–$C_6$alkylcarbonyl-$C_2$–$C_6$alkynyl, cyano-$C_2$–$C_6$alkynyl, nitro-$C_2$–$C_6$alkynyl, $C_3$–$C_6$halocycloalkyl, hydroxy-$C_1$–$C_6$alkyl, $C_1$–$C_6$alkoxy-$C_1$–$C_6$alkyl, $C_1$–$C_6$alkylthio-$C_1$–$C_6$alkyl, cyano, $C_1$–$C_4$alkylcarbonyl, $C_1$–$C_6$alkoxycarbonyl, hydroxy, $C_1$–$C_6$alkoxy, $C_3$–$C_6$alkenyloxy, $C_3$–$C_6$alkynyloxy, $C_1$–$C_6$haloalkoxy, $C_3$–$C_6$haloalkenyloxy, $C_1$–$C_6$alkoxy-$C_1$–$C_6$alkoxy, mercapto, $C_1$–$C_6$alkylthio, $C_1$–$C_6$haloalkylthio, $C_1$–$C_6$alkylsulfinyl, $C_1$–$C_6$alkylsulfonyl, nitro, amino, $C_1$–$C_6$alkylamino, di($C_1$–$C_6$alkyl)amino or phenoxy in which the phenyl ring may be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_2$ also may be phenyl, naphthyl or a 5- or 6-membered aromatic ring that may contain 1 or 2 hetero atoms selected from the group consisting of nitrogen, oxygen and sulfur, wherein the phenyl ring, the naphthyl ring system and the 5- or 6-membered aromatic ring may be substituted by halogen, $C_3$–$C_8$cycloalkyl, hydroxy, mercapto, amino, cyano, nitro or by formyl; and/or the phenyl ring, the naphthyl ring system and the 5- or 6-membered aromatic ring may be substituted by $C_1$–$C_6$alkyl, $C_1$–$C_6$alkoxy, hydroxy-$C_1$–$C_6$alkyl, $C_1$–$C_6$alkoxy-$C_1$–$C_6$alkyl, $C_1$–$C_6$alkoxy-$C_1$–$C_6$alkoxy, $C_1$–$C_6$alkylcarbonyl, $C_1$–$C_6$alkylthio, $C_1$–$C_6$alkylsulfinyl, $C_1$–$C_6$alkylsulfonyl, mono-$C_1$–$C_6$alkylamino, di($C_1$–$C_6$alkyl)amino, $C_1$–$C_6$alkylcarbonylamino, $C_1$–$C_6$alkylcarbonyl-($C_1$–$C_6$alkyl)amino, $C_2$–$C_6$alkenyl, $C_3$–$C_6$alkenyloxy, hydroxy-$C_3$–$C_6$alkenyl, $C_1$–$C_6$alkoxy-$C_2$–$C_6$alkenyl, $C_1$–$C_6$alkoxy-$C_3$–$C_6$alkenyloxy, $C_2$–$C_6$alkenylcarbonyl, $C_2$–$C_6$alkenylthio, $C_2$–$C_6$alkenylsulfinyl, $C_2$–$C_6$alkenylsulfonyl, mono- or di-($C_2$–$C_6$alkenyl)amino, $C_1$–$C_6$alkyl($C_3$–$C_6$alkenyl)amino, $C_2$–$C_6$alkenylcarbonylamino, $C_2$–$C_6$alkenylcarbonyl($C_1$–$C_6$alkyl)amino, $C_2$–$C_6$alkynyl, $C_3$–$C_6$alkynyloxy, hydroxy-$C_3$–$C_6$alkynyl, $C_1$–$C_6$alkoxy-$C_3$–$C_6$alkynyl, $C_1$–$C_6$alkoxy-$C_4$–$C_6$alkynyloxy, $C_2$–$C_6$alkynylcarbonyl, $C_2$–$C_6$alkynylthio, $C_2$–$C_6$alkynylsulfinyl, $C_2$–$C_6$alkynylsulfonyl or di-($C_3$–$C_6$alkynyl)amino, $C_1$–$C_6$alkyl($C_3$–$C_6$alkynyl)amino, $C_2$–$C_6$alkynylcarbonylamino or by $C_2$–$C_6$alkynylcarbonyl($C_1$–$C_6$alkyl)amino; and/or the phenyl ring, the naphthyl ring system and the 5- or 6-membered aromatic ring may be substituted by halo-substituted $C_1$–$C_6$alkyl, $C_1$–$C_6$alkoxy, hydroxy-$C_1$–$C_6$alkyl, $C_1$–$C_6$alkoxy-$C_1$–$C_6$alkyl, $C_1$–$C_6$alkoxy-$C_1$–$C_6$alkoxy, $C_1$–$C_6$alkylcarbonyl, $C_1$–$C_6$alkylthio, $C_1$–$C_6$alkylsulfinyl, $C_1$–$C_6$alkylsulfonyl, mono-$C_1$–$C_6$alkylamino, di($C_1$–$C_6$alkyl)amino, $C_1$–$C_6$alkylcarbonylamino, $C_1$–$C_6$alkylcarbonyl($C_1$–$C_6$alkyl)amino, $C_2$–$C_6$alkenyl, $C_3$–$C_6$alkenyloxy, hydroxy-$C_3$–$C_6$alkenyl, $C_1$–$C_6$alkoxy-$C_2$–$C_6$alkenyl, $C_1$–$C_6$alkoxy-$C_3$–$C_6$alkenyloxy, $C_2$–$C_6$alkenylcarbonyl, $C_2$–$C_6$alkenylthio, $C_2$–$C_6$alkenylsulfinyl, $C_2$–$C_6$alkenylsulfonyl, mono- or di-($C_2$–$C_6$alkenyl)amino, $C_1$–$C_6$alkyl-($C_3$–$C_6$alkenyl)amino, $C_2$–$C_6$alkenylcarbonylamino, $C_2$–$C_6$alkenylcarbonyl($C_1$–$C_6$alkyl)amino, $C_2$–$C_6$alkynyl, $C_3$–$C_6$alkynyloxy, hydroxy-$C_3$–$C_6$alkynyl, $C_1$–$C_6$alkoxy-$C_3$–$C_6$alkynyl, $C_1$–$C_6$alkoxy-$C_4$–$C_6$alkynyloxy, $C_2$–$C_6$alkynylcarbonyl, $C_2$–$C_6$alkynylthio, $C_2$–$C_6$alkynylsulfinyl, $C_2$–$C_6$alkynylsulfonyl, mono- or di-($C_3$–$C_6$alkynyl)amino, $C_1$–$C_6$alkyl($C_3$–$C_6$alkynyl)amino, $C_2$–$C_6$alkynylcarbonylamino or $C_2$–$C_6$alkynylcarbonyl($C_1$–$C_6$alkyl)amino; and/or the phenyl ring, the naphthyl ring system and the 5- or 6-membered aromatic ring may be substituted by a radical of the formula $COOR_{50}$, $CONR_{51}$, $SO_2NR_{53}R_{54}$ or $SO_2OR_{55}$ wherein $R_{50}$, $R_{51}$, $R_{52}$, $R_{53}$, $R_{54}$ and $R_{55}$ are each independently of the others $C_1$–$C_6$alkyl, $C_2$–$C_6$alkenyl or $C_3$–$C_6$alkynyl or halo-, hydroxy-, alkoxy-, mercapto-, amino-, cyano-, nitro-, alkylthio-, alkylsulfinyl- or alkylsulfonyl-substituted $C_1$–$C_6$alkyl, $C_2$–$C_6$alkenyl or $C_3$–$C_6$alkynyl;

n is 0, 1 or 2;

$R_4$ and $R_5$ are each independently of the other hydrogen, $C_1$–$C_{12}$alkyl, $C_1$–$C_{12}$haloalkyl, $C_2$–$C_8$alkenyl, $C_2$–$C_8$alkynyl, $C_1$–$C_{10}$alkoxy-$C_1$–$C_8$alkyl, poly-$C_1$–$C_{10}$alkoxy-$C_1$–$C_8$alkyl, $C_1$–$C_{10}$alkylthio-$C_1$–$C_8$alkyl, $C_3$–$C_8$cycloalkyl, $C_3$–$C_8$halocycloalkyl, 4- to 8-membered heterocyclyl, phenyl, α- or β-naphthyl, phenyl-$C_1$–$C_6$alkyl, α- or β-naphthyl-$C_1$–$C_6$alkyl, 5- or 6-membered heteroaryl or 5- or 6-membered heteroaryl-$C_1$–$C_6$alkyl, wherein those aromatic and heteroaromatic rings may be substituted by halogen, $C_1$–$C_6$alkyl, $C_1$–$C_6$haloalkyl, $C_1$–$C_6$alkoxy, $C_1$–$C_6$haloalkoxy, nitro or by cyano; or $R_4$ and $R_5$, together with the nitrogen atoms to which they are bonded, form a saturated or unsaturated 5- to 8-membered heterocyclic ring that 1) may be interrupted by oxygen, sulfur or by —$NR_{14}$— and/or may be substituted by halogen, $C_1$–$C_{10}$alkyl, $C_1$–$C_{10}$haloalkyl, hydroxy, $C_1$–$C_6$alkoxy, $C_1$–$C_6$alkoxy-$C_1$–$C_6$alkoxy, $C_1$–$C_6$haloalkoxy, mercapto, $C_1$–$C_6$alkylthio, $C_3$–$C_7$cycloalkyl, heteroaryl, heteroaryl-$C_1$–$C_6$alkyl, phenyl, phenyl-$C_1$–$C_6$alkyl or by benzyloxy, wherein the phenyl rings of the last three substituents may in turn be substituted by halogen, $C_1$–$C_6$alkyl, $C_1$–$C_6$haloalkyl, $C_1$–$C_6$alkoxy, $C_1$–$C_6$haloalkoxy or by nitro, and/or 2) may contain a fused or spiro-bound alkylene or alkenylene chain having from 2 to 6 carbon atoms that is optionally interrupted by oxygen or by sulfur, or at least one ring atom of the saturated or unsaturated heterocyclic ring bridges that alkylene or alkenylene chain; $R_{14}$ is hydrogen, $C_1$–$C_4$alkyl, $C_1$–$C_6$alkylcarbonyl, $C_1$–$C_6$alkylsulfonyl, $C_3$–$C_6$alkenyl or $C_3$–$C_6$alkynyl; and G is hydrogen, a metal ion equivalent or an ammonium, sulfonium or phosphonium cation, which comprises reacting a compound of formula II:

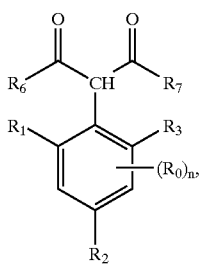

(II)

wherein $R_0$, $R_1$, $R_2$, $R_3$ and n are as defined hereinbefore; $R_6$ is $R_8R_9N$—; $R_7$ is $R_{10}R_{11}N$— or $R_{12}O$—; and $R_8$, $R_9$, $R_{10}$, $R_{11}$ and $R_{12}$ are each independently of the others hydrogen, $C_1$–$C_6$alkyl, $C_1$–$C_6$haloalkyl, $C_3$–$C_6$alkenyl or benzyl, wherein the phenyl ring of the benzyl group may be substituted by $C_1$–$C_4$alkyl, halogen, $C_1$–$C_4$haloalkyl, $C_1$–$C_4$alkoxy or by nitro, in an inert organic solvent, optionally in the presence of a base, with a compound of formula IV, IVa or IVb:

(IV)

(IVa)

(IVb)

wherein $R_4$ and $R_5$ are as defined hereinbefore and He·Hal is a hydrogen halide, and optionally converting the resulting compound of formula I wherein G is a metal ion equivalent or an ammonium cation, by salt conversion into the corresponding salt of formula I wherein G is a sulfonium or phosphonium cation, or by treatment with a Brönsted acid into the corresponding compound of formula I wherein G is hydrogen.

The present invention relates also to the direct ('in situ') conversion, in a one-pot reaction, of compounds of formula I to compounds of formula Ia:

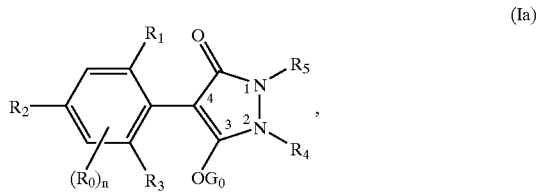

(Ia)

wherein $R_0$, $R_1$, $R_2$, $R_3$, $R_4$, $R_5$ and n are as defined for formula I;

$G_0$ is a group —$C(O)$—$R_{30}$, —$C(X_1)$—$X_2$—$R_{31}$, —$C(X_3)$—$N(R_{32})$—$R_{33}$, —$SO_2$—$R_{34}$ or —$P(X_4)(R_{35})$—$R_{36}$;

$X_1$, $X_2$, $X_3$ and $X_4$ are each independently of the others oxygen or sulfur;

$R_{30}$ is unsubstituted or halo-substituted $C_1$–$C_{20}$alkyl, $C_2$–$C_{20}$alkenyl, $C_1$–$C_8$alkoxy-$C_1$–$C_8$alkyl, $C_1$–$C_8$alkylthio-$C_1$–$C_8$alkyl, poly-$C_1$–$C_8$alkoxy-$C_1$–$C_8$alkyl or unsubstituted or halo-, $C_1$–$C_6$alkyl- or $C_1$–$C_6$alkoxy-substituted $C_3$–$C_8$cycloalkyl, in which optionally at least one ring member has been replaced by oxygen and/or by sulfur, $C_3$–$C_6$cycloalkyl-$C_1$–$C_6$alkyl, heterocyclyl-$C_1$–$C_6$alkyl, heteroaryl-$C_1$–$C_6$alkyl, unsubstituted or halo-, cyano-, nitro-, $C_1$–$C_6$alkyl-, $C_1$–$C_6$alkoxy-, $C_1$–$C_6$haloalkyl-, $C_1$–$C_6$haloalkoxy-, $C_1$–$C_6$alkylthio- or $C_1$–$C_6$alkylsulfonyl-substituted phenyl, unsubstituted or halo-, nitro-, cyano-, $C_1$–$C_6$alkyl-, $C_1$–$C_6$alkoxy-, $C_1$–$C_6$haloalkyl- or $C_1$–$C_6$haloalkoxy-substituted phenyl-$C_1$–$C_6$alkyl, unsubstituted or halo- or $C_1$–$C_6$alkyl-substituted heteroaryl, unsubstituted or halo- or $C_1$–$C_6$alkyl-substituted phenoxy-$C_1$–$C_6$alkyl, or unsubstituted or halo-, amino- or $C_1$–$C_6$alkyl-substituted heteroaryloxy-$C_1$–$C_6$alkyl;

$R_{31}$ is unsubstituted or halo-substituted $C_1$–$C_{20}$alkyl, $C_2$–$C_{20}$alkenyl, $C_1$–$C_8$alkoxy-$C_2$–$C_8$alkyl, poly- $C_1$–$C_8$alkoxy-$C_2$–$C_8$alkyl, unsubstituted or halo-, $C_1$–$C_6$alkyl- or $C_1$–$C_6$alkoxy-substituted $C_3$–$C_8$cycloalkyl, $C_3$–$C_6$cycloalkyl-$C_1$–$C_6$alkyl, heterocyclyl-$C_1$–$C_6$alkyl, heteroaryl-$C_1$–$C_6$alkyl, unsubstituted or halo-, cyano-, nitro-, $C_1$–$C_6$alkyl-, $C_1$–$C_6$alkoxy-, $C_1$–$C_6$haloalkyl- or $C_1$–$C_6$haloalkoxy-substituted phenyl or benzyl;

$R_{32}$ and $R_{33}$ are each independently of the other hydrogen, unsubstituted or halo-substituted $C_1$–$C_8$alkyl, $C_3$–$C_8$cycloalkyl, $C_1$–$C_8$alkoxy, $C_3$–$C_8$alkenyl, $C_1$–$C_8$alkoxy-$C_1$–$C_8$alkyl, unsubstituted or halo-, $C_1$–$C_8$haloalkyl-, $C_1$–$C_8$alkyl- or $C_1$–$C_8$alkoxy-substituted phenyl or benzyl; or $R_{32}$ and $R_{33}$ together form a $C_3$–$C_6$alkylene chain in which a carbon atom has optionally been replaced by oxygen or by sulfur;

$R_{34}$ is unsubstituted or halo-substituted $C_1$–$C_8$alkyl, $C_3$–$C_8$alkenyl, $C_3$–$C_8$haloalkenyl, $C_3$–$C_8$alkynyl, $C_3$–$C_8$haloalkynyl, or unsubstituted or halo-, $C_1$–$C_6$alkyl-, $C_1$–$C_6$alkoxy-, $C_1$–$C_4$haloalkyl-, $C_1$–$C_4$haloalkoxy-, cyano- or nitro-substituted phenyl or benzyl;

$R_{35}$ and $R_{36}$ are each independently of the other unsubstituted or halo-substituted $C_1$–$C_8$alkyl, $C_1$–$C_8$alkoxy, $C_1$–$C_8$alkylamino, di($C_1$–$C_8$alkyl)amino, $C_1$–$C_8$alkylthio, $C_2$–$C_8$alkenylthio, $C_3$–$C_7$cycloalkylthio, or unsubstituted or halo-, nitro-, cyano-, $C_1$–$C_4$alkoxy-, $C_1$–$C_4$haloalkoxy-, $C_1$–$C_4$alkylthio-, $C_1$–$C_4$haloalkylthio-, $C_1$–$C_4$alkyl- or $C_1$–$C_4$haloalkyl-substituted phenyl, phenoxy or phenylthio, which conversion comprises reacting compounds of formula I, optionally in the presence of an acid-binding agent or a catalyst, with an electrophile of formula XII or XIId:

$$G_0\text{—}L \quad \text{(XII) or}$$

$$R_{32}\text{—}N\text{=}C\text{=}X_3 \quad \text{(XIId),}$$

wherein $G_0$, $R_{32}$ and $X_3$ are as defined hereinbefore except that $R_{32}$ is not hydrogen, and L is a leaving group, for example $R_{30}C(O)O\text{—}$, $R_{31}X_2\text{—}$ or halogen, preferably chlorine, bromine or iodine.

Depending on the substituents $R_0$ to $R_5$, G and $G_0$, the compounds of formulae I and Ia may be in the form of geometric and/or optical isomers or isomeric mixtures (atropisomers) and, when G is hydrogen, a metal ion equivalent, or an ammonium, sulfonium or phosphonium cation, they may be in the form of tautomers or tautomeric mixtures.

If the starting materials employed are not enantiomerically pure, the compounds of formulae I and Ia obtained in the above-described processes are generally in the form of racemates or diastereoisomeric mixtures which, if desired, can be separated on the basis of their physico-chemical properties according to known methods, such as, for example, fractional crystallisation following salt formation with optically pure bases, acids or metal complexes, or by chromatographic procedures, such as, for example, high-pressure liquid chromatography (HPLC) on acetyl cellulose.

In the present invention, the compounds of formulae I and Ia are to be understood as both the enriched and optically pure forms of the respective stereoisomers as well as the racemates and diastereoisomers. Unless there is specific reference to the individual optical antipodes, the given formulae are to be understood as the racemic mixtures that have been obtained by the preparation process according to the invention. When an aliphatic C=C double bond is present, geometric isomerism may also occur.

The present invention relates also to the salts that the compounds of formulae I and Ia are able to form with acids. Suitable acids for the formation of the acid addition salt include both organic and inorganic acids. Examples of such acids are hydrochloric acid, hydrobromic acid, nitric acid, phosphoric acids, sulfuric acid, acetic acid, propionic acid, butyric acid, valeric acid, oxalic acid, malonic acid, fumaric acid, organic sulfonic acids, lactic acid, tartaric acid, citric acid and salicylic acid.

In view of their acidity, the compounds of formula I wherein G is hydrogen can readily be converted in the presence of bases (proton acceptors) into the corresponding salts (wherein G is, for example, a metal ion equivalent or an ammonium cation), as described, for example, in EP-A-0 508 126. Any customary proton acceptor may be used as base. The salts are, for example, alkali metal salts, for example sodium and potassium salts; alkaline earth metal salts, for example calcium and magnesium salts; ammonium salts, that is to say, unsubstituted ammonium salts and mono- or poly-substituted ammonium salts, for example triethylammonium and methylammonium salts, or salts with other organic bases or other cations, for example sulfonium or phosphonium cations. Sulfonium cations include, for example, tri($C_1$–$C_4$alkyl)sulfonium cations, which can be obtained from the corresponding alkali metal salts, for example, by salt conversion, for example using a cation exchanger.

Among the alkali metal and alkaline earth metal hydroxides as salt formers, special mention may be made, for example, of the hydroxides of lithium, sodium, potassium, magnesium and calcium, but especially the hydroxides of sodium and potassium. Suitable salt formers are described, for example, in WO 97/41112.

Examples of suitable amines for ammonium salt formation include both ammonia and primary, secondary and tertiary $C_1$–$C_{18}$alkylamines, $C_1$–$C_4$-hydroxyalkylamines and $C_2$–$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylaminei octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, N-methylmorpholine, thiomorpholine, piperidine, pyrrolidine, indoline, quinuclidine and azepine; primary arylamines, for example anilines, methoxyanilines, ethoxy-anilines, o-, m- and p-toluidines, phenylenediamines, benzidines, naphthylamines and o-, m- and p-chloroanilines; but especially triethylamine, isopropylamine and diisopropylamine.

In the above definitions, halogen is to be understood as fluorine, chlorine, bromine or iodine, preferably fluorine, chorine or bromine.

The alkyl groups occurring in the substituent definitions are, for example, methyl, ethyl, n-propyl, isopropyl, n-butyl, sec-butyl, isobutyl or tert-butyl, and the pentyl, hexyl, heptyl, octyl, nonyl, decyl, undecyl and dodecyl isomers.

Haloalkyl groups preferably have a chain length of from 1 to 6 carbon atoms. Haloalkyl is, for example, fluoromethyl, difluoromethyl, difluorochloromethyl, trifluoromethyl, chloromethyl, dichloromethyl, dichlorofluoromethyl, trichloromethyl, 2,2,2-trifluoroethyl, 2-fluoroethyl, 2-chloroethyl, 2,2-difluoroethyl, 2,2-dichloroethyl, 2,2,2-trichloroethyl or pentafluoroethyl, preferably trichloromethyl, difluoromethyl, difluorochloromethyl, trifluoromethyl or dichlorofluoromethyl.

Alkoxy groups preferably have a chain length of from 1 to 6 carbon atoms. Alkoxy is, for example, methoxy, ethoxy, n-propoxy, isopropoxy, n-butoxy, isobutoxy, sec-butoxy, tertbutoxy or a pentyloxy or hexyloxy isomer, preferably methoxy, ethoxy or n-propoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

There may be mentioned as examples of alkenyl radicals vinyl, allyl, methallyl, 1-methylvinyl, but-2-en-1-yl, pentenyl and 2-hexenyl; preferably alkenyl radicals having a chain length of from 3 to 6 carbon atoms.

There may be mentioned as examples of alkynyl radicals ethynyl, propargyl, 1-methyl-propargyl, 3-butynyl, but-2-yn-1-yl, 2-methylbut-3-yn-2-yl, but-3-yn-2-yl, 1-pentynyl, pent-4-yn-1-yl and 2-hexynyl; preferably alkynyl radicals having a chain length of from 3 to 6 carbon atoms.

Suitable haloalkenyl radicals include alkenyl groups substituted one or more times by halogen, halogen being in particular bromine or iodine and especially fluorine or chlorine, for example 2- and 3-fluoropropenyl, 2- and 3-chloropropenyl, 2- and 3-bromopropenyl, 2,2-di-fluoro-1-methylvinyl, 2,3,3-trifluoropropenyl, 3,3,3-trifluoropropenyl, 2,3,3-trichloropropenyl, 4,4,4-trifluorobut-2-en-1-yl and 4,4,4-trichlorobut-2-en-1-yl. Preferred alkenyl radicals substituted once, twice or three times by halogen are those having a chain length of from 3 to 6 carbon atoms. The alkenyl groups may be substituted by halogen at saturated or unsaturated carbon atoms.

Suitable haloalkynyl groups include, for example, alkynyl groups substituted one or more times by halogen, halogen being bromine or iodine and especially fluorine or chlorine, for example 3-fluoropropynyl, 3-chloropropynyl, 3-bromopropynyl and 4,4,4-trifluorobut-2-yn-1-yl.

Alkenyloxy is, for example, allyloxy, methallyloxy or but-2-en-1-yloxy.

Alkynyloxy is, for example, propargyloxy or 1-methylpropargyloxy.

Suitable haloalkenyloxy groups include alkenyloxy groups substituted one or more times by halogen, halogen being in particular bromine or iodine and especially fluorine or chlorine, for example 2- and 3-fluoropropenyloxy, 2- and 3-chloropropenyloxy, 2- and 3-bromopropenyloxy, 2,3,3-trifluoropropenyloxy, 2,3,3-trichloropropenyloxy, 4,4,4-trifluorobut-2-en-1-yloxy and 4,4,4-trichlorobut-2-en-1-yloxy.

Alkoxyalkyl groups have preferably from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

Polyalkoxy-alkyl is, for example, methoxymethoxy-methyl, ethoxymethoxy-methyl, ethoxy-ethoxy-methyl, n-propoxyethoxy-methyl, isopropoxyethoxy-methyl, methoxymethoxy-ethyl, ethoxymethoxy-ethyl, ethoxyethoxy-ethyl, n-propoxyethoxy-methyl, n-propoxyethoxy-ethyl, isopropoxyethoxy-methyl, isopropoxyethoxy-ethyl or (ethoxy)$_3$-ethyl.

Suitable cycloalkyl substituents contain from 3 to 8 carbon atoms and are, for example, cyclopropyl, cyclobutyl, cyclopentyl, cyclohexyl, cycloheptyl or cyclooctyl. They may be substituted one or more times by halogen, preferably fluorine, chlorine and/or bromine.

Alkylcarbonyl is especially acetyl or propionyl.

Alkoxycarbonyl is, for example, methoxycarbonyl, ethoxycarbonyl, n-propoxycarbonyl, isopropoxycarbonyl or a butoxycarbonyl, pentyloxycarbonyl or hexyloxycarbonyl isomer, preferably methoxycarbonyl or ethoxycarbonyl.

Phenyl, phenoxy and naphthyl may be in substituted form, in which case the substituents may, as desired, be in the ortho-, meta- and/or para-position and, in the case of the naphthyl ring system, in addition in the 5-, 6-, 7- and/or 8-position. Preferred positions for the substituents are the ortho- and para-position to the ring attachment point. Where the phenyl, phenoxy and naphthyl substituents are not explicitly mentioned they are, for example, $C_1$–$C_4$alkyl, halogen, $C_1$–$C_6$haloalkyl, $C_1$–$C_6$alkoxy, $C_1$–$C_6$haloalkoxy, nitro, cyano, amino, $C_1$–$C_4$alkylamino or di($C_1$–$C_4$alkyl)amino.

Alkylthio groups preferably have a chain length of from 1 to 6 carbon atoms. Alkylthio is, for example, methylthio, ethylthio, propylthio, butylthio, pentylthio or hexylthio, or a branched isomer thereof, but is preferably methylthio or ethylthio.

Haloalkylthio is, for example, 2,2,2-trifluoroethylthio or 2,2,2-trichloroethylthio.

Alkylsulfinyl is, for example, methylsulfinyl, ethylsulfinyl, n-propylsulfinyl, isopropylsulfinyl, n-butylsulfinyl, isobutylsulfinyl, sec-butylsulfinyl or tert-butylsulfinyl; preferably methylsulfinyl or ethylsulfinyl.

Alkylsulfonyl is, for example, methylsulfonyl, ethylsulfonyl, n-propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or a butyl-, pentyl- or hexyl-amine isomer.

Dialkylamino is, for example, dimethylamino, methylethylamino, diethylamino, n-propylmethylamino, dibutylamino or diisopropylamino.

Alkylthioalkyl is, for example, methylthiomethyl, methylthioethyl, ethylthiomethyl, ethylthioethyl, n-propylthiomethyl, n-propylthioethyl, isopropylthiomethyl or isopropylthioethyl.

Heterocyclyl radicals are preferably 4- to 8-membered rings that contain 1 or 2 hetero atoms, for example N, S and/or O. They are usually saturated.

Heteroaryl radicals are usually 5- or 6-membered aromatic heterocycles that contain preferably from 1 to 3 hetero atoms, such as N, S and/or O. The following are examples of suitable heterocyclyl and heteroaryl radicals: pyridyl, pyrrolidyl, piperidyl, pyranyl, dioxanyl, azetidyl, oxetanyl, pyrimidyl, triazinyl, thiazolyl, triazolyl, thiadiazolyl, imidazolyl, oxazolyl, isoxazolyl, pyrazinyl, furyl, thienyl, morpholyl, piperazinyl, pyrazolyl, benzoxazolyl, benzothiazolyl, quinoxalyl, indolyl and quinolyl. Those heterocycles and heteroaromatic radicals may in addition be substituted, the substituents, where they are not explicitly mentioned, being, for example, halogen, $C_1$–$C_6$alkyl, $C_1$–$C_6$alkoxy, $C_1$–$C_6$haloalkyl, $C_1$–$C_6$haloalkoxy, $C_1$–$C_6$alkylthio, amino, $C_1$–$C_6$alkylamino, di($C_1$–$C_6$alkyl)amino, phenyl, nitro or cyano.

The substituent definition according to which "$R_4$ and $R_5$, together with the nitrogen atoms to which they are bonded, form a saturated or unsaturated, 5- to 8-membered heterocyclic ring that 1) may be interrupted by oxygen, sulfur or by —$NR_{14}$— and/or may be substituted by halogen, $C_1$–$C_{10}$alkyl, $C_1$–$C_{10}$haloalkyl, hydroxy, $C_1$–$C_6$alkoxy, $C_1$–$C_6$alkoxy-$C_1$–$C_6$alkoxy, $C_1$–$C_6$haloalkoxy, mercapto, $C_1$–$C_6$alkylthio, $C_3$–$C_7$cyploalkyl, heteroaryl, heteroaryl-$C_1$–$C_6$alkyl, phenyl, phenyl-$C_1$–$C_6$alkyl or by benzyloxy, wherein the phenyl rings of the last three substituents may in turn be substituted by halogen, $C_1$–$C_6$alkyl, $C_1$–$C_6$haloalkyl, $C_1$–$C_6$alkoxy, $C_1$–$C_6$haloalkoxy or by nitro, and/or 2) may contain a fused or spiro-bound alkylene or alkenylene chain having from 2 to 6 carbon atoms that is optionally interrupted by oxygen or by sulfur, or at least one ring atom of the saturated or unsaturated heterocyclic ring bridges that alkylene or alkenylene chain", signifies, for example, the following heterocyclic ring systems:

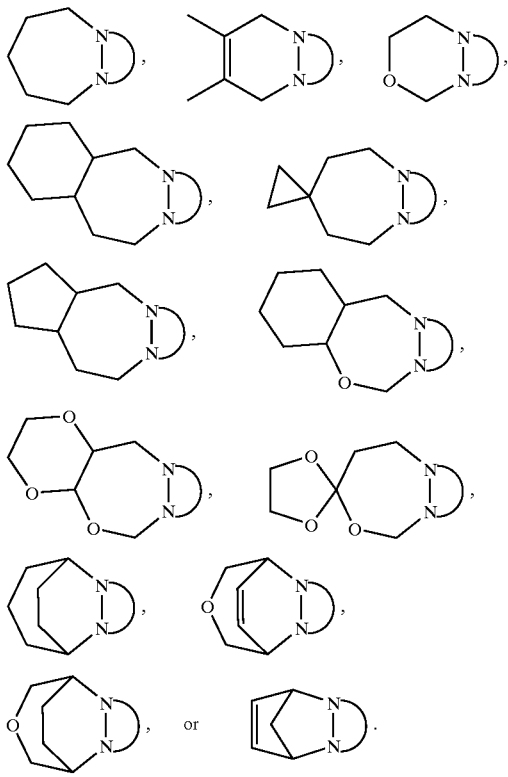

In the above polycyclic rings systems, the abbreviated representation

denotes the group

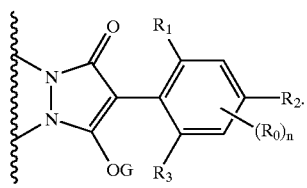

The 5- to 8-membered heterocyclic rings that the substituents $R_4$ and $R_5$ together may form and the fused or spiro-bound alkylene or alkenylene chains having from 2 to 6 carbon atoms may accordingly be interrupted once or twice by hetero atoms, such as, for example, oxygen.

Meanings corresponding to those given hereinbefore can also be ascribed to the substituents in composite definitions, such as, for example, alkoxy-alkoxy, alkylsulfonylamino, alkyl-aminosulfonyl, alkoxy-carbonyl, alkyl-carbonylamino, phenyl-alkyl, naphthyl-alkyl and heteroaryl-alkyl.

In the definitions of alkylcarbonyl, alkylcarbonylamino and alkoxycarbonyl, the carbon atom of the carbonyl is not included in the lower and upper limits given for the number of carbon atoms in each particular case.

The composite definitions that may arise in respect of the radicals $R_{30}$, $R_3$, and $R_{34}$ in substituent $G_0$ in formula Ia, such as, for example, cycloalkyl-thio, cycloalkyl-alkyl, heterocyclyl-alkyl, heteroaryl-alkyl, phenyl-alkyl, phenoxy-alkyl and heteroaryloxy-alkyl radicals, are derived from the corresponding radicals of the radicals mentioned above. Heterocyclyl radicals are preferably those containing 1 or 2 hetero atoms, such as, for example, N, S and O. They are usually saturated.

Heteroaryl radicals are usually aromatic heterocycles that contain preferably from 1 to 3 hetero atoms, such as N, S and/or O. Such heterocycles and heteroaromatic radicals may furthermore be substituted, for example by halogen, $C_1$–$C_4$alkyl and/or amino. The $C_2$–$C_{20}$alkenyl groups represented by $R_{31}$ may be mono- or poly-unsaturated. They contain preferably from 2 to 12, especially from 2 to 6, carbon atoms.

The definition of the electrophile G—L of formula XII includes the following electrophiles: L—C(O)—$R_{30}$ (XIIa), L—C($X_1$)—$X_2$—$R_{31}$ (XIIb), L—C($X_3$)—N($R_{32}$)—$R_{33}$ (XIIc), $R_{32}$N=C=$X_3$(XIId), L—$SO_2$—$R_{34}$ (XIIe) and L—P($X_4$)($R_{35}$)—$R_{36}$ (XIIf).

In the electrophile of formula XII, L is a leaving group, such as, for example, $R_{30}$C(O)O— or $R_{31}$O— (wherein $R_{30}$ and $R_3$ are as defined for formula Ia), or halogen, preferably chlorine, bromine or iodine.

The process according to the invention is especially well suited to the preparation of compounds of formula I wherein $R_0$ is, each independently of any other, halogen, $C_1$–$C_6$alkyl, $C_1$–$C_6$haloalkyl, hydroxy, $C_1$–$C_6$alkoxy, nitro, amino, $C_1$–$C_6$alkylamino, di($C_1$–$C_6$alkyl)amino, $C_1$–$C_6$alkylcarbonylamino, $C_1$–$C_6$alkylsulfonylamino, $C_1$–$C_6$alkylaminosulfonyl, $C_1$–$C_4$alkylcarbonyl, $C_1$–$C_6$alkoxycarbonyl or carboxy; and $R_1$, $R_2$ and $R_3$ are each independently of the others hydrogen, halogen, $C_1$–$C_6$alkyl, $C_2$–$C_6$alkenyl, $C_2$–$C_6$alkynyl, $C_3$–$C_6$cycloalkyl, $C_1$–$C_6$haloalkyl, $C_2$–$C_6$haloalkenyl, $C_2$–$C_6$haloalkynyl, $C_3$–$C_6$halocycloalkyl, $C_1$–$C_6$alkoxy-$C_1$–$C_6$alkyl, $C_1$–$C_6$alkylthio-$C_1$–$C_6$alkyl, cyano, $C_1$–$C_4$alkylcarbonyl, $C_1$–$C_6$alkoxycarbonyl, hydroxy, $C_1$–$C_{10}$alkoxy, $C_3$–$C_6$alkenyloxy, $C_3$–$C_6$alkynyloxy, $C_1$–$C_6$haloalkoxy, $C_3$–$C_6$haloalkenyloxy, $C_1$–$C_6$alkoxy-$C_1$–$C_6$alkoxy, mercapto, $C_1$–$C_6$alkylthio, $C_1$–$C_6$haloalkylthio, $C_1$–$C_6$alkylsulfinyl, $C_1$–$C_6$alkylsulfonyl, nitro, amino, $C_1$–$C_4$alkylamino or di($C_1$–$C_4$alkyl)amino.

The process according to the invention is especially well suited also to the preparation of compounds of formula I wherein $R_1$, $R_2$ and $R_3$ are each independently of the others hydrogen, halogen, $C_1$–$C_4$alkyl, $C_2$–$C_4$alkenyl, $C_2$–$C_4$alkynyl, $C_1$–$C_4$haloalkyl, $C_3$- or $C_4$-haloalkenyl, $C_3$–$C_6$cycloalkyl, $C_1$–$C_4$alkylcarbonyl, $C_1$–$C_6$alkoxycarbonyl, hydroxy, $C_1$–$C_4$alkoxy, $C_3$- or $C_4$-alkenyloxy, $C_3$- or $C_4$-alkynyloxy, $C_1$–$C_4$haloalkoxy, nitro or amino.

The process according to the invention is especially well suited also to the preparation of compounds of formula I wherein $R_4$ and $R_5$, together with the nitrogen atoms to which they are bonded, form a saturated or unsaturated, 6- or 7-membered heterocyclic ring that 1) may be interrupted once by oxygen or by sulfur and/or 2) may contain a fused or spiro-bound alkylene chain having from 2 to 5 carbon atoms that is optionally interrupted once or twice by oxygen or by sulfur, or at least one ring atom of the saturated or unsaturated heterocyclic ring bridges that alkylene chain.

In a preferred variant of the process according to the invention, there are preferably used compounds of formula II wherein $R_8$, $R_9$, $R_{10}$, $R_{11}$ and $R_{12}$ are hydrogen, $C_1$–$C_6$alkyl or benzyl.

The preparation of the compounds of formulae I and Ia is explained in detail in the following Reaction Schemes 1 and 2.

Reaction Scheme 1

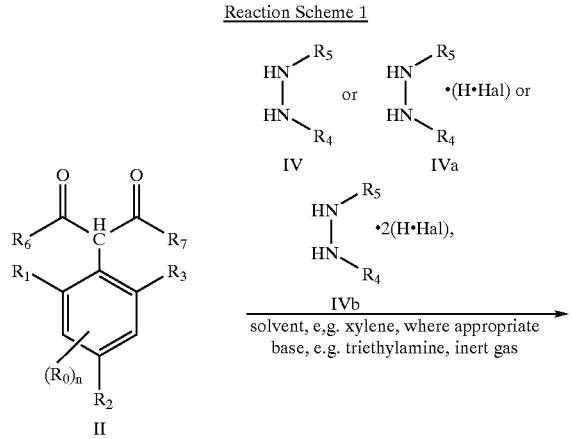

solvent, e.g. xylene, where appropriate base, e.g. triethylamine, inert gas

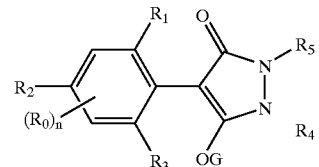

I:(G=H, alkali metal ion, alkaline earth metal ion, ammonium cation)

The compounds of formulae II and IV, IVa or IVb can be used in equimolar amounts, but an excess of from 5 to 50 mol % of the compound of formula IV, IVa or IVb can be of advantage.

The reaction of compounds of formula II with compounds of formula IV, IVa or IVb is carried out at a reaction temperature of from 0° to 200° C., a temperature range of from 80° C. to 150° C. being preferred.

Suitable inert organic solvents for the reaction of compounds of formula II with compounds of formula IV, IVa or IVb are, for example, aromatic, aliphatic and cycloaliphatic hydrocarbons, for example, benzene, toluene, the xylene isomers ortho-, meta- and para-xylene, cyclohexane and methylcyclohexane; halogenated hydrocarbons, for example chlorobenzene and the dichlorobenzene isomers 1,2-, 1,3- and 1,4-dichlorobenzene; ethers, for example dibutyl ether, tert-butyl methyl ether, 1,2-dimethoxyethane (DME), ethylene glycol dimethyl ether, diethylene glycol dimethyl ether, 1,3-dioxolane and dioxane; nitriles, for example acetonitrile, propionitrile and benzonitrile; dialkyl sulfoxides, for example dimethyl sulfoxide (DMSO); amides and lactams, for example N,N-dimethylformamide (DMF), N,N-diethylformamide and N-methylpyrrolidone (NMP); alcohols, glycols (diols) and polyalcohols, for example propanol, butanol, cyclohexanol, ethylene glycol and 2-ethoxyethanol, and also, generally, carboxylic acids, for example acetic acid and propionic acid, or mixtures of those solvents.

Preference is given to those organic solvents having a boiling point $\geq 80°$ C., especially a boiling point $\geq 100°$ C.

Special preference is given to toluene, the xylene isomers ortho-, meta- and para-xylene, methylcyclohexane, chlorobenzene and the dichlorobenzene isomers 1,2-, 1,3- and 1,4-dichlorobenzene.

The reaction according to the invention is preferably carried out in an inert gas atmosphere, for example in a nitrogen or argon gas atmosphere.

The condensation of compounds of formula II with compounds of formula IV can be carried out with or without the addition of a base. The same condensation reaction carried out with compounds of formula IVa or IVb (instead of compounds of formula IV) is advantageously carried out in the presence of a base. Suitable bases in that case include, for example, nitrogen bases generally, for example tertiary amines and pyridines, for example $C_1$–$C_6$trialkylamines, quinuclidine and 4-dimethylaminopyridine. Further suitable bases are, for example, alkali metal alcoholates, for example sodium and potassium methanolate, sodium and potassium ethanolate and sodium and potassium tert-butanolate. It is also possible to use inorganic bases, for example alkali metal and alkaline earth metal hydrides, such as sodium, potassium or calcium hydride, hydroxides, such as sodium or potassium hydroxide, carbonates, such as sodium or potassium carbonate, and hydrogen carbonates, such as sodium or potassium hydrogen carbonate, especially in the form of solutions in alcohol. Such bases are used in catalytic amounts or in a molar excess of up to 5 based on the compound of formula II.

In a preferred embodiment of the process according to the invention, an aromatic hydrocarbon having a boiling point >80° C., for example xylene, is used as the reaction medium in which the reactants of formulae II and IV, IVa or IVb are dissolved. Preferably, the compound of formula IV, IVa or IVb is used in an excess of from 5 to 20 mol % based on the compound of formula II. The reaction mixture is heated at reflux temperature for from 1 to 3 hours in an inert gas atmosphere, with or without the addition of a base when a compound of. formula IV is used, and in the presence of an equimolar amount or an up to 5-fold excess of an organic base, such as triethylamine, when a compound of formula IVa or IVb is used. After cooling and the addition of dilute acid, the desired product (G=hydrogen) precipitates in the form of a crystalline solid and can be filtered off directly and washed with a suitable washing agent, for example water and/or hexane.

The compounds of formula I wherein $R_0$, $R_1$, $R_2$, $R_3$, $R_4$, $R_5$ and n are as defined hereinbefore and G is hydrogen, a metal ion equivalent or an ammonium cation can readily be converted into the compounds of formula Ia either a) in accordance with the invention, directly in the reaction solution in a one-pot reaction, without isolation, or b) in a subsequent reaction step, after having been isolated, by means of reaction, optionally in the presence of an acid-binding agent or a catalyst, with an electrophile of formula XII wherein $G_0$ is as defined hereinbefore and L is a leaving group, for example $R_{30}C(O)O$— or $R_{31}O$— (wherein $R_{30}$ and $R_{31}$, are as defined for formula Ia), or halogen, preferably chlorine, bromine or iodine. Reaction Scheme 2 illustrates that derivatisation step.

Reaction Scheme 2

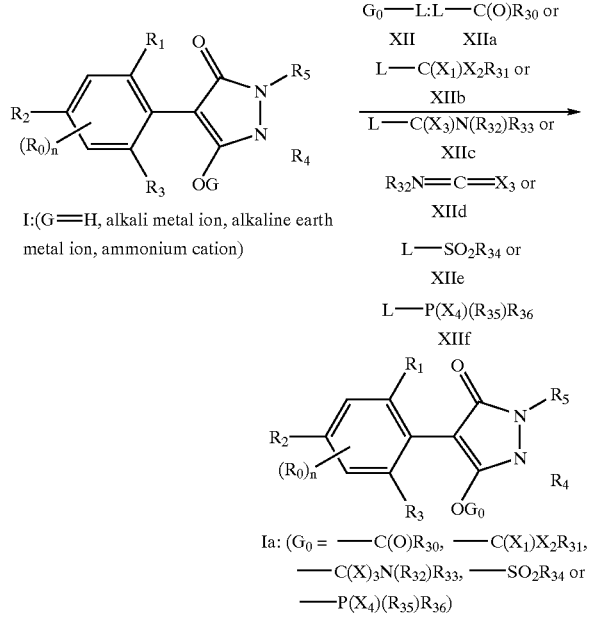

The acid-binding agents that may be used for the reaction of a compound of formula I with an electrophile of formula XII may be conventional proton acceptors, for example alkali metal hydrides, alkali metal alcoholates, alkali metal or alkaline earth metal carbonates or hydrogen carbonates, or nitrogen bases generally, for example triethylamine, diisopropylamine, pyridine, quinoline, diazabicyclononene (DBN) and diazabicycloundecene (DBU). There may be added as catalysts for the reaction of a compound of formula I with an electrophile of formula lid catalysts that accelerate the reaction, for example organotin compounds, for example dibutyltin dilaurate.

The solvents used may be any that are inert with respect to the electrophiles of formulae XII and XIIa to XIIf, for example aromatic hydrocarbons, for example benzene, toluene or a xylene isomer; halogenated hydrocarbons, for example dichloromethane, trichloromethane, chlorobenzene or a dichlorobenzene isomer; amides, for example N,N-dimethylformamide (DMF) or 1-methyl-2-pyrrolidone (NMP); or ethers, for example dibutyl ether, 1,2-dimethoxyethane (DME), 1,3-dioxolane, tetrahydrofuran or dioxane.

Analogous reactions of compounds of formula I wherein G is hydrogen in accordance with the above variant b), that is to say, as a separate reaction step, are described, for example, in WO 97/02243 and EP-A-0 508 126.

The compounds of formula I prepared in accordance with the invention wherein G is hydrogen, a metal ion equivalent or an ammonium, sulfonium or phosphonium cation are therefore used especially as starting compounds for the 'in situ' preparation of compounds of formula Ia wherein $G_0$ is a group —C(O)—$R_{30}$, —C($X_1$)—$X_2$—$R_{31}$, —C($X_3$)—N($R_{32}$)—$R_{33}$, —SO$_2$—$R_{34}$ or —P($X_4$)($R_{35}$)—$R_{36}$; and $R_{30}$, $R_{31}$, $R_{32}$, $R_{33}$, $R_{34}$, $R_{35}$, $R_{36}$, $X_1$, $X_2$, $X_3$ an $X_4$ are as defined for formula Ia.

The compounds of formula I:

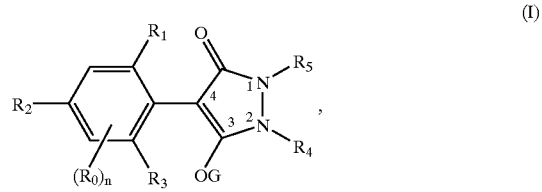

(I)

wherein $R_0$ is, each independently of any other, halogen, $C_1$–$C_6$alkyl, $C_2$–$C_6$alkenyl, $C_2$–$C_6$alkynyl, $C_1$–$C_6$haloalkyl, cyano-$C_1$–$C_6$alkyl, $C_2$–$C_6$haloalkenyl, cyano-$C_2$–$C_6$alkenyl, $C_2$–$C_6$haloalkynyl, cyano-$C_2$–$C_6$alkynyl, hydroxy, hydroxy-$C_1$–$C_6$alkyl, $C_1$–$C_6$alkoxy, nitro, amino, $C_1$–$C_6$alkylamino, di($C_1$–$C_6$alkyl)amino, $C_1$–$C_6$alkylcarbonylamino, $C_1$–$C_6$alkylsulfonylamino, $C_1$–$C_6$alkylaminosulfonyl, $C_1$–$C_6$alkylcarbonyl, $C_1$–$C_6$alkylcarbonyl-$C_1$–$C_6$alkyl, $C_1$–$C_6$alkoxycarbonyl-$C_1$–$C_6$alkyl, $C_1$–$C_6$alkylcarbonyl-$C_2$–$C_6$alkenyl, $C_1$–$C_6$alkoxycarbonyl-$C_2$–$C_6$alkenyl, $C_1$–$C_6$alkylcarbonyl-$C_2$–$C_6$alkynyl, $C_1$–$C_6$alkoxycarbonyl-$C_2$–$C_6$alkynyl, $C_1$–$C_6$alkoxycarbonyl, cyano, carboxyl, phenyl or an aromatic ring that contains 1 or 2 hetero atoms selected from the group consisting of nitrogen, oxygen and sulfur, wherein the latter two aromatic rings may be substituted by $C_1$–$C_3$alkyl, $C_1$–$C_3$haloalkyl, $C_1$–$C_3$alkoxy, $C_1$–$C_3$haloalkoxy, halogen, cyano or by nitro; or $R_0$, together with the adjacent substituents $R_1$, $R_2$ and $R_3$, forms a saturated or unsaturated $C_3$–$C_6$hydrocarbon bridge that may be interrupted by 1 or 2 hetero atoms selected from the group consisting of nitrogen, oxygen and sulfur and/or may be substituted by $C_1$–$C_4$alkyl; $R_1$, $R_2$ and $R_3$ are each independently of the others hydrogen, halogen, $C_1$–$C_6$alkyl, $C_2$–$C_6$alkenyl, $C_2$–$C_6$alkynyl, $C_3$–$C_6$cycloalkyl, $C_1$–$C_6$haloalkyl, $C_2$–$C_6$haloalkenyl, $C_1$–$C_6$alkoxycarbonyl-$C_2$–$C_6$alkenyl, $C_1$–$C_6$alkylcarbonyl-$C_2$–$C_6$alkenyl, cyano-$C_2$–$C_6$alkenyl, nitro-$C_2$–$C_6$alkenyl, $C_2$–$C_6$haloalkynyl, $C_1$–$C_6$alkoxycarbonyl-$C_2$–$C_6$alkynyl, $C_1$–$C_6$alkylcarbonyl-$C_2$–$C_6$alkynyl, cyano-$C_2$–$C_6$alkynyl, nitro-$C_2$–$C_6$alkynyl, $C_3$–$C_6$-halocycloalkyl, hydroxy-$C_1$–$C_6$alkyl, $C_1$–$C_6$alkoxy-$C_1$–$C_6$alkyl, $C_1$–$C_6$alkylthio-$C_1$–$C_6$alkyl, cyano, $C_1$–$C_4$alkylcarbonyl, $C_1$–$C_6$alkoxycarbonyl, hydroxy, $C_1$–$C_{10}$alkoxy, $C_3$–$C_6$alkenyloxy, $C_3$–$C_6$alkynyloxy, $C_1$–$C_6$haloalkoxy, $C_3$–$C_6$haloalkenyloxy, $C_1$–$C_6$alkoxy-$C_1$–$C_6$alkoxy, mercapto, $C_1$–$C_6$alkylthio, $C_1$–$C_6$halolkylthio, $C_1$–$C_6$alkylsulfinyl, $C_1$–$C_6$alkylsulfonyl, nitro, amino, $C_1$–$C_6$alkylamino, di($C_1$–$C_6$alkyl)amino or phenoxy in which the phenyl ring may be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_2$ also may be phenyl, naphthyl or a 5- or 6-membered aromatic ring that may contain 1 or 2 hetero atoms selected from the group consisting of nitrogen, oxygen and sulfur, wherein the phenyl ring, the naphthyl ring system and the 5- or 6-membered aromatic ring may be substituted by halogen, $C_3$–$C_8$cycloalkyl, hydroxy, mercapto, amino, cyano, nitro or by formyl; and/or the phenyl ring, the naphthyl ring system and the 5- or 6-membered aromatic ring may be substituted by $C_1$–$C_6$alkyl, $C_1$–$C_6$alkoxy, hydroxy-$C_1$–$C_6$alkyl, $C_1$–$C_6$alkoxy-$C_1$–$C_6$alkyl, $C_1$–$C_6$alkoxy-$C_1$–$C_6$alkoxy, $C_1$–$C_6$alkylcarbonyl, $C_1$–$C_6$alkylthio, $C_1$–$C_6$alkylsultinyl, $C_1$–$C_6$alkylsulfonyl, mono-$C_1$–$C_6$alkylamino, di($C_1$–$C_6$alkyl)amino, $C_1$–$C_6$alkylcarbonylamino, $C_1$–$C_6$alkylcarbonyl-($C_1$–$C_6$alkyl)amino, $C_2$–$C_6$alkenyl, $C_3$–$C_6$alkenyloxy, hydroxy-$C_3$–$C_6$alkenyl, $C_1$–$C_6$alkoxy-$C_2$–$C_6$alkenyl, $C_1$–$C_6$alkoxy-$C_3$–$C_6$alkenyloxy, $C_2$–$C_6$alkenylcarbonyl, $C_2$–$C_6$alkenylthio, $C_2$–$C_6$alkenylsulfinyl, $C_2$–$C_6$alkenylsulfonyl, mono- or di-($C_2$–$C_6$alkenyl)amino, $C_1$–$C_6$alkyl($C_3$–$C_6$alkenyl)amino, $C_2$–$C_6$alkenylcarbonylamino, $C_2$–$C_6$alkenylcarbonyl($C_1$–$C_6$alkyl)amino, $C_2$–$C_6$alkynyl, $C_3$–$C_6$alkynyloxy, hydroxy-$C_3$–$C_6$alkynyl, $C_1$–$C_6$alkoxy-$C_3$–$C_6$alkynyl, $C_1$–$C_6$alkkoxy-$C_4$–$C_6$alkynyloxy, $C_2$–$C_6$alkynylcarbonyl, $C_2$–$C_6$alkynylthio, $C_2$–$C_6$alkynylsulfinyl, $C_2$–$C_6$alkynylsulfonyl, mono- or di-($C_3$–$C_6$alkynyl)amino, $C_1$–$C_6$alkyl($C_3$–$C_6$alkynyl)amino, $C_2$–$C_6$alkynylcarbonylamino or by $C_2$–$C_6$alkynylcarbonyl($C_1$–$C_6$alkyl)amino; and/or the phenyl ring, the naphthyl ring system and the 5- or 6-membered aromatic ring may be substituted by halo-substituted $C_1$–$C_6$alkyl, $C_1$–$C_6$alkoxy, hydroxy-$C_1$–$C_6$alkyl, $C_1$–$C_6$alkoxy-$C_1$–$C_6$alkyl, $C_1$–$C_6$alkoxy-$C_1$–$C_6$alkoxy, $C_1$–$C_6$alkylcarbonyl, $C_1$–$C_6$alkylthio, $C_1$–$C_6$alkyls $C_1$–$C_6$alkylsulfonyl, mono-$C_1$–$C_6$alkylamino, di($C_1$–$C_6$alkyl)amino, $C_1$–$C_6$alkylcarbonylamino, $C_1$–$C_6$alkylcarbonyl($C_1$–$C_6$alkyl)amino, $C_2$–$C_6$alkenyl, $C_3$–$C_6$alkenyloxy, hydroxy-$C_3$–$C_6$alkenyl, $C_1$–$C_6$alkoxy-$C_2$–$C_6$alkenyl, $C_1$–$C_6$alkoxy-$C_3$–$C_6$alkenyloxy, $C_2$–$C_6$alkenylcarbonyl, $C_2$–$C_6$alkenylthio, $C_2$–$C_6$alkenylsulfinyl, $C_2$–$C_6$alkenylsulfonyl, mono- or di-($C_2$–$C_6$alkenyl)amino, $C_1$–$C_6$alkyl-($C_3$–$C_6$alkenyl)amino, $C_2$–$C_6$alkenylcarbonylamino, $C_2$–$C_6$alkenylcarbonyl($C_1$–$C_6$alkyl)amino, $C_2$–$C_6$alkynyl, $C_3$–$C_6$alkynyloxy, hydroxy-$C_3$–$C_6$alkynyl, $C_1$–$C_6$alkoxy-$C_3$–$C_6$alkynyl, $C_1$–$C_6$alkoxy-$C_4$–$C_6$alkynyloxy, $C_2$–$C_6$alkynylcarbonyl, $C_2$–$C_6$alkynylthio, $C_2$–$C_6$alkynylsulfinyl, $C_2$–$C_6$alkynylsulfonyl, mono- or di-($C_3$–$C_6$alkynyl)amino, $C_1$–$C_6$alkyl($C_3$–$C_6$alkynyl)amino, $C_2$–$C_6$alkynylcarbonylamino or $C_2$–$C_6$alkynylcarbonyl($C_1$–$C_6$alkyl)amino; and/or the phenyl ring, the naphthyl ring system and the 5- or 6-membered aromatic ring may be substituted by a radical of the formula $COOR_{50}$, $CONR_{51}$, $SO_2NR_{53}R_{54}$ or $SO_2OR_{55}$ wherein $R_{50}$, $R_{51}$, $R_{52}$, $R_{53}$, $R_{54}$ and $R_5$ are each independently of the others $C_1$–$C_6$alkyl, $C_2$–$C_6$alkeny or $C_3$–$C_6$alkynyl or halo-, hydroxy-, alkoxy-, mercapto-, amino-, cyano-, nitro-, alkylthio-, alkyl-sulfinyl- or alkylsulfonyl-substituted $C_1$–$C_6$alkyl, $C_2$–$C_6$alkenyl or $C_3$–$C_6$alkynyl; n is 1 or 2; $R_4$ and $R_5$, together with the nitrogen atoms to which they are bonded, form a saturated or unsaturated 5- to 8-membered heterocyclic ring that 1) is interrupted by oxygen, sulfur or by —$NR_{14}$— and may be substituted by halogen, $C_1$–$C_{10}$alkyl, $C_1$–$C_{10}$haloalkyl, hydroxy, $C_1$–$C_6$alkoxy, $C_1$–$C_6$alkoxy-$C_1$–$C_6$alkoxy, $C_1$–$C_6$haloalkoxy, mercapto, $C_1$–$C_6$alkylthio, $C_3$–$C_7$cycloalkyl, heteroaryl, heteroaryl-$C_1$–$C_6$alkyl, phenyl, phenyl-$C_1$–$C_6$alkyl or by benzyloxy, wherein the phenyl rings of the last three substituents may in turn be substituted by halogen, $C_1$–$C_6$alkyl, $C_1$–$C_6$haloalkyl, $C_1$–$C_6$alkoxy, $C_1$–$C_6$haloalkoxy or by nitro, and 2) may contain a fused or spiro-bound alkylene or alkenylene chain having from 2 to 6 carbon atoms that is optionally interrupted by oxygen or by sulfur, or at least one ring atom of the saturated or unsaturated heterocyclic ring bridges that alkylene or alkenylene chain; $R_{14}$ is hydrogen, $C_1$–$C_4$alkyl, $C_1$–$C_6$alkylcarbonyl, $C_1$–$C_6$alkylsulfonyl, $C_3$–$C_6$alkenyl or $C_3$–$C_6$alkynyl; and G is hydrogen or a metal ion equivalent or an ammonium, sulfonium or phosphonium cation, are new. The present invention accordingly relates also to those compounds.

The compounds of formula Ia

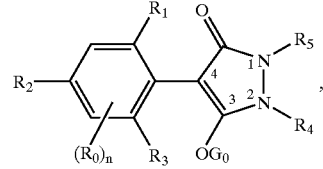

(Ia)

wherein $R_0$ is, each independently of any other, halogen, $C_1$–$C_6$alkyl, $C_2$–$C_6$alkenyl, $C_2$–$C_6$alkynyl, $C_1$–$C_6$haloalkyl, cyano-$C_1$–$C_6$alkyl, $C_2$–$C_6$haloalkenyl, cyano-$C_2$–$C_6$alkenyl, $C_2$–$C_6$haloalkynyl, cyano-$C_2$–$C_6$alkynyl, hydroxy, hydroxy-$C_1$–$C_6$alkyl, $C_1$–$C_6$alkoxy, nitro, amino, $C_1$–$C_6$alkylamino, di($C_1$–$C_6$alkyl)amino, $C_1$–$C_6$alkylcarbonylamino, $C_1$–$C_6$alkylsulfonylamino, $C_1$–$C_6$alkylaminosulfonyl, $C_1$–$C_6$alkylcarbonyl, $C_1$–$C_6$alkylcarbonyl-$C_1$–$C_6$alkyl, $C_1$–$C_6$alkoxycarbonyl-$C_1$–$C_6$alkyl, $C_1$–$C_6$alkylcarbonyl-$C_2$–$C_6$alkenyl, $C_1$–$C_6$alkoxycarbonyl-$C_2$–$C_6$alkenyl, $C_1$–$C_6$alkylcarbonyl-$C_2$–$C_6$alkynyl, $C_1$–$C_6$alkoxycarbonyl-$C_2$–$C_6$alkynyl, $C_1$–$C_6$alkoxycarbonyl, cyano, carboxyl, phenyl or an aromatic ring that contains 1 or 2 hetero atoms selected from the group consisting of nitrogen, oxygen and sulfur, wherein the latter two aromatic rings may be substituted by $C_1$–$C_3$alkyl, $C_1$–$C_3$haloalkyl, $C_1$–$C_3$alkoxy, $C_1$–$C_3$haloalkoxy, halogen, cyano or by nitro; or $R_0$, together with the adjacent substituents $R_1$, $R_2$ and $R_3$, forms a saturated or unsaturated $C_3$–$C_6$hydrocarbon bridge that may be interrupted by 1 or 2 hetero atoms selected from the group consisting of nitrogen, oxygen and sulfur and/or may be substituted by $C_1$–$C_4$alkyl; $R_1$, $R_2$ and $R_3$ are each independently of the others hydrogen, halogen, $C_1$–$C_6$alkyl, $C_2$–$C_6$alkenyl, $C_2$–$C_6$alkynyl, $C_3$–$C_6$cycloalkyl, $C_1$–$C_6$haloalkyl, $C_2$–$C_6$haloalkenyl, $C_1$–$C_6$alkoxycarbbnyl-$C_2$–$C_6$alkenyl, $C_1$–$C_6$alkylcarbonyl-$C_2$–$C_6$alkenyl, cyano-$C_2$–$C_6$alkenyl, nitro-$C_2$–$C_6$alkenyl, $C_2$–$C_6$haloalkynyl, $C_1$–$C_6$alkoxycarbonyl-$C_2$–$C_6$alkynyl, $C_1$–$C_6$alkylcarbonyl-$C_2$–$C_6$alkynyl, cyano-$C_2$–$C_6$alkynyl, nitro-$C_2$–$C_6$alkynyl, $C_3$–$C_6$halocycloalkyl, hydroxy-$C_1$–$C_6$alkyl, $C_1$–$C_6$alkoxy-$C_1$–$C_6$alkyl, $C_1$–$C_6$alkylthio-$C_1$–$C_6$alkyl, cyano, $C_1$–$C_4$alkylcarbonyl, $C_1$–$C_6$alkoxycarbonyl, hydroxy, $C_1$–$C_6$alkoxy, $C_3$–$C_6$alkenyloxy, $C_3$–$C_6$alkynyloxy, $C_1$–$C_6$haloalkoxy, $C_3$–$C_6$haloalkenyloxy, $C_1$–$C_6$alkoxy-$C_1$–$C_6$alkoxy, mercapto, $C_1$–$C_6$alkylthio, $C_1$–$C_6$haloalkylthio, $C_1$–$C_6$alkylsulfinyl, $C_1$–$C_6$alkylsulfonyl, nitro, amino, $C_1$–$C_6$alkylamino, di-($C_1$–$C_6$alkyl)amino or phenoxy in which the phenyl ring may be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_2$ also may be phenyl, naphthyl or a 5- or 6-membered aromatic ring that may contain 1 or 2 hetero atoms selected from the group consisting of nitrogen, oxygen and sulfur, wherein the phenyl ring, the naphthyl ring system and the 5- or 6-membered aromatic ring may be substituted by halogen, $C_3$–$C_8$cycloalkyl, hydroxy, mercapto, amino, cyano, nitro or by formyl; and/or the phenyl ring, the naphthyl ring system and the 5- or 6-membered aromatic ring may be substituted by $C_1$–$C_6$alkyl, $C_1$–$C_6$alkoxy, hydroxy-$C_1$–$C_6$alkyl, $C_1$–$C_6$alkoxy-$C_1$–$C_6$alkyl, $C_1$–$C_6$-alkoxy-$C_1$–$C_6$alkoxy, $C_1$–$C_6$alkylcarbonyl, $C_1$–$C_6$alkylthio, $C_1$–$C_6$alkylsulfinyl, $C_1$–$C_6$alkylsulfonyl, mono-$C_1$–$C_6$alkylamino, di($C_1$–$C_6$alkyl)amino, $C_1$–$C_6$alkylcarbonylamino, $C_1$–$C_6$alkylcarbonyl-($C_1$–$C_6$alkyl)amino, $C_2$–$C_6$alkenyl, $C_3$–$C_6$alkenyloxy, hydroxy-$C_3$–$C_6$alkenyl, $C_1$–$C_6$alkoxy-$C_2$–$C_6$alkenyl, $C_1$–$C_6$alkoxy-$C_3$–$C_6$alkenyloxy, $C_2$–$C_6$alkenylcarbonyl, $C_2$–$C_6$alkenylthio, $C_2$–$C_6$alkenyl-sulfinyl, $C_2$–$C_6$alkenylsulfonyl, mono- or di-($C_2$–$C_6$alkenyl)amino, $C_1$–$C_6$alkyl($C_3$–$C_6$alkenyl)amino, $C_2$–$C_6$alkenylcarbonylamino, $C_2$–$C_6$alkenylcarbonyl($C_1$–$C_6$alkyl)amino, $C_2$–$C_6$alkynyl, $C_3$–$C_6$alkynyloxy, hydroxy-$C_3$–$C_6$alkynyl, $C_1$–$C_6$alkoxy-$C_3$–$C_6$alkynyl, $C_1$–$C_6$alkoxy-$C_4$–$C_6$alkynyloxy, $C_2$–$C_6$alkynylcarbonyl, $C_2$–$C_6$alkynylthio, $C_2$–$C_6$alkynylsulfinyl, $C_2$–$C_6$alkynylsulfonyl, mono- or di-($C_3$–$C_6$alkynyl)amino, $C_1$–$C_6$alkyl($C_3$–$C_6$alkynyl)amino, $C_2$–$C_6$alkynylcarbonylamino or by $C_2$–$C_6$alkynylcarbonyl($C_1$–$C_6$alkyl)amino; and/or the phenyl ring, the naphthyl ring system and the 5- or 6-membered aromatic ring may be substituted by halo-substituted $C_1$–$C_6$alkyl, $C_1$–$C_6$alkoxy, hydroxy-$C_1$–$C_6$alkyl, $C_1$–$C_6$alkoxy-$C_1$–$C_6$alkyl, $C_1$–$C_6$alkoxy-$C_1$–$C_6$alkoxy, $C_1$–$C_6$alkylcarbonyl, $C_1$–$C_6$alkylthio, $C_1$–$C_6$alkylsulfinyl, $C_1$–$C_6$alkylsulfonyl, mono-$C_1$–$C_6$alkylamino, di($C_1$–$C_6$alkyl)amino, $C_1$–$C_6$alkylcarbonylamino, $C_1$–$C_6$alkylcarbonyl($C_1$–$C_6$alkyl)amino, $C_2$–$C_6$alkenyl, $C_3$–$C_6$alkenyloxy, hydroxy-$C_3$–$C_6$alkenyl, $C_1$–$C_6$alkoxy-$C_2$–$C_6$alkenyl, $C_1$–$C_6$alkoxy-$C_3$–$C_6$alkenyloxy, $C_2$–$C_6$alkenylcarbonyl, $C_2$–$C_6$alkenylthio, $C_2$–$C_6$alkenylsulfinyl, $C_2$–$C_6$alkenylsulfonyl, mono- or di-($C_2$–$C_6$alkenyl)amino, $C_1$–$C_6$alkyl-($C_3$–$C_6$alkenyl)amino, $C_2$–$C_6$alkenylcarbonylamino, $C_2$–$C_6$alkenylcarbonyl($C_1$–$C_6$alkyl)amino, $C_2$–$C_6$alkynyl, $C_3$–$C_6$alkynyloxy, hydroxy-$C_3$–$C_6$alkynyl, $C_1$–$C_6$alkoxy-$C_3$–$C_6$alkynyl, $C_1$–$C_6$alkoxy-$C_4$–$C_6$alkynyloxy, $C_2$–$C_6$alkynylcarbonyl, $C_2$–$C_6$alkynylthio, $C_2$–$C_6$alkynylsulfinyl, $C_2$–$C_6$alkynylsulfonyl, mono- or di-($C_3$–$C_6$alkynyl)amino, $C_1$–$C_6$alkyl($C_3$–$C_6$alkynyl)amino, $C_2$–$C_6$alkynylcarbonylamino or $C_2$–$C_6$alkynylcarbonyl($C_1$–$C_6$alkyl)amino; and/or the phenyl ring, the naphthyl ring system and the 5- or 6-membered aromatic ring may be substituted by a radical of the formula $COOR_{50}$, $CONR_{51}$, $SO_2NR_{53}R_{54}$ or $SO_2OR_{55}$ wherein $R_{50}$, $R_{51}$, $R_{52}$, $R_{53}$, $R_{54}$ and $R_{55}$ are each independently of the others $C_1$–$C_6$alkyl, $C_2$–$C_6$alkenyl or $C_3$–$C_6$alkynyl or halo-, hydroxy-, alkoxy-, mercapto-, amino-, cyano-, nitro-, alkylthio-, alkylsulfinyl- or alkylsulfonyl-substituted $C_1$–$C_6$alkyl, $C_2$–$C_6$alkenyl or $C_3$–$C_6$alkynyl;

n is 1 or 2;

$R_4$ and $R_5$, together with the nitrogen atoms to which they are bonded, form a saturated or unsaturated 5- to 8-membered heterocyclic ring that 1) is interrupted by oxygen, sulfur or by —$NR_{14}$— and may be substituted by halogen, $C_1$–$C_{10}$alkyl, $C_1$–$C_{10}$haloalkyl, hydroxy, $C_1$–$C_6$alkoxy, $C_1$–$C_6$alkoxy-$C_1$–$C_6$alkoxy, $C_1$–$C_6$haloalkoxy, mercapto, $C_1$–$C_6$alkylthio, $C_3$–$C_7$Cycloalkyl, heteroaryl, heteroaryl-$C_1$–$C_6$alkyl, phenyl, phenyl-$C_1$–$C_6$alkyl or by benzyloxy, wherein the phenyl rings of the last three substituents may in turn by substituted by halogen, $C_1$–$C_6$alkyl, $C_1$–$C_6$haloalkyl, $C_1$–$C_6$alkoxyl $C_1$–$C_6$haloalkoxy or by nitro, and 2) may contain a fused or spiro-bound alkylene or alkenylene chain having from 2 to 6 carbon atoms that is optionally interrupted by oxygen or by sulfur, or at least one ring atom of the saturated or unsaturated heterocyclic ring bridges that alkylene or alkenylene chain; $R_{14}$ is hydrogen, $C_1$–$C_4$alkyl, $C_1$–$C_6$alkylcarbonyl, $C_1$–$C_6$alkylsulfonyl, $C_3$–$C_6$alkenyl or $C_3$–$C_6$alkynyl; and $G_0$ is a group —C(O)—$R_{30}$, —C($X_1$)—$X_2$—$R_{31}$ or —$SO_2$—$R_{34}$;

$X_1$, $X_2$, $X_3$ and $X_4$ are each independently of the others oxygen or sulfur; $R_{30}$ is unsubstituted or halo-substituted $C_1$–$C_{20}$alkyl, $C_2$–$C_{20}$alkenyl, $C_1$–$C_8$alkoxy-$C_1$–$C_8$alkyl, $C_1$–$C_8$alkylthio-$C_1$–$C_8$alkyl, poly-$C_1$–$C_8$alkoxy-$C_1$–$C_8$alkyl or unsubstituted or halo-substituted $C_3$–$C_8$cycloalkyl, $C_3$–$C_6$cycloalkyl-$C_1$–$C_6$alkyl, heterocyclyl-$C_1$–$C_6$alkyl, heteroaryl-$C_1$–$C_6$alkyl, unsubstituted or halo-, cyano-, nitro-, $C_1$–$C_6$alkyl-, $C_1$–$C_6$alkoxy-, $C_1$–$C_6$haloalkyl-, $C_1$–$C_6$haloalkoxy-, $C_1$–$C_6$alkylthio- or $C_1$–$C_6$alkylsulfonyl-substituted phenyl, unsubstituted or halo-, nitro-, cyano-, $C_1$–$C_6$alkyl-, $C_1$–$C_6$alkoxy-, $C_1$–$C_6$haloalkyl- or $C_1$–$C_6$haloalkoxy-substituted phenyl-$C_1$–$C_6$alkyl, unsubstituted or halo- or $C_1$–$C_6$alkyl-substituted heteroaryl, unsubstituted or halo- or $C_1$–$C_6$alkyl-substituted phenoxy-$C_1$–$C_6$alkyl, or unsubstituted or halo-, amino- or $C_1$–$C_6$alkyl-substituted heteroaryloxy-$C_1$–$C_6$alkyl; $R_{31}$ is unsubstituted or halo-substituted $C_1$–$C_{20}$alkyl, $C_2$–$C_{20}$alkenyl, $C_1$–$C_8$alkoxy-$C_2$–$C_8$alkyl, poly-$C_1$–$C_8$alkoxy-$C_2$–$C_8$alkyl, unsubstituted or halo- or $C_1$–$C_6$alkoxy-substituted $C_3$–$C_8$cycloalkyl, $C_3$–$C_6$cycloalkyl-$C_1$–$C_6$alkyl, heterocyclyl-$C_1$–$C_6$alkyl, heteroaryl-$C_1$–$C_6$alkyl, unsubstituted or halo-, cyano-, nitro-, $C_1$–$C_6$alkyl-, $C_1$–$C_6$alkoxy-, $C_1$–$C_6$haloalkyl- or $C_1$–$C_6$haloalkoxy-substituted phenyl or benzyl; and $R_{34}$ is unsubstituted or halo-substituted $C_1$–$C_8$alkyl, or unsubstituted or halo-, $C_1$–$C_6$alkyl-, $C_1$–$C_6$alkoxy-, $C_1$–$C_4$haloalkyl-, $C_1$–$C_4$haloalkoxy-, cyano- or nitro-substituted phenyl, are new. The present invention accordingly relates also to those compounds.

The compounds of formula II:

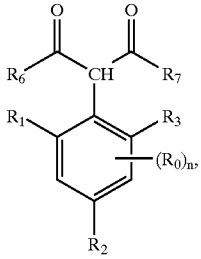

(II)

wherein $R_0$, $R_1$, $R_2$, $R_3$, $R_6$, $R_7$ and n are as defined hereinbefore are new and were developed especially for the process according to the invention. The present invention accordingly relates also to those compounds.

Preferred compounds of formula II are those wherein $R_1$, $R_2$ and $R_3$ are each independently of the others hydrogen, halogen, $C_1$–$C_4$alkyl, $C_1$–$C_4$haloalkyl, $C_2$–$C_4$alkenyl, $C_2$–$C_4$haloalkenyl, $C_2$–$C_4$alkynyl, $C_3$–$C_6$cycloalkyl, $C_1$–$C_4$alkylcarbonyl, $C_1$–$C_6$alkoxycarbonyl, hydroxy, $C_1$–$C_4$alkoxy, $C_3$- or $C_4$-alkenyloxy, $C_3$- or $C_4$-alkynyloxy, $C_1$–$C_4$haloalkoxy, nitro or amino.

Preference is given also to compounds of formula II wherein $R_1$ is $C_2$–$C_6$alkyl.

Likewise preferred are compounds of formula II wherein n is 0.

Of those, special preference is given to compounds of formula II wherein $R_1$ is $C_2$–$C_4$alkyl, $C_1$–$C_4$alkoxy, $C_2$–$C_4$alkynyl or $C_3$–$C_6$cycloalkyl and $R_3$ is $C_1$–$C_4$alkyl, $C_1$–$C_4$alkoxy, $C_2$–$C_4$alkynyl or $C_3$–$C_6$cycloalkyl.

Likewise preferred are compounds of formula II wherein $R_1$ is $C_2$–$C_6$alkynyl.

Preference is given to those compounds of formula II wherein $R_1$ and $R_3$ are each independently of the other $C_2$–$C_6$alkyl, $C_2$–$C_6$alkynyl, $C_1$–$C_{10}$Dalkoxy or $C_3$–$C_6$cycloalkyl. Of those, special preference is given to the compounds wherein $R_1$ is $C_2$–$C_6$alkyl and $R_3$ is $C_2$–$C_6$alkyl, $C_2$–$C_6$alkynyl or $C_1$–$C_{10}$alkoxy.

Also important are the compounds of formula II wherein $R_6$ is $R_8R_9N$— and $R_7$ is $R_{10}R_{11}N$—; $R_8$, $R_9$, $R_{10}$ and $R_{11}$ being as defined for formula II.

The compounds of formula IIa

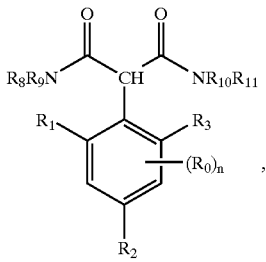

(IIa)

wherein $R_0$, $R_1$, $R_2$, $R_3$ and n are as defined for formula II and $R_8$, $R_9$, $R_{10}$ and $R_{11}$ are hydrogen, can be obtained, for example, directly from the corresponding phenylmalonic acid dinitriles of formula VI:

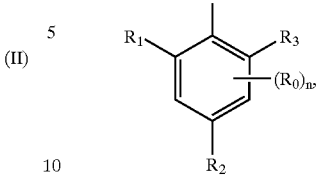

(VI)

wherein $R_0$, $R_1$, $R_2$, $R_3$ and n are as defined hereinbefore, by means of hydrolysis. Concentrated mineral acids, for example, sulfuric acid or nitric acid, are suitable as hydrolysing agents, where appropriate with the addition of water.

The compounds of formula IIa:

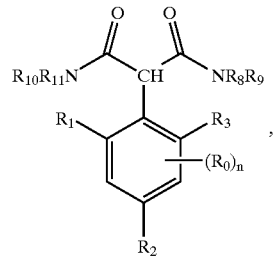

(IIa)

wherein $R_0$, $R_1$, $R_2$, $R_3$ and n are as defined for formula I and $R_8$, $R_9$, $R_{10}$ and $R_{11}$ are each independently of the others hydrogen, $C_1$–$C_6$alkyl, $C_1$–$C_6$haloalkyl, $C_3$–$C_6$alkenyl or benzyl, wherein the phenyl ring of the benzyl group may be substituted by $C_1$–$C_4$alkyl, halogen, $C_1$–$C_4$haloalkyl, $C_1$–$C_4$alkoxy or by nitro, can be prepared, for example, as follows:

1) a phenyl acetamide of formula VII:

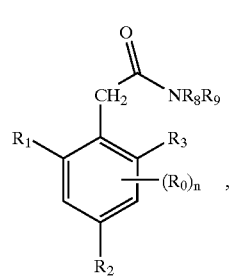

(VII)

wherein $R_0$, $R_1$, $R_2$, $R_3$, $R_8$, $R_9$ and n are as defined hereinbefore, is either a) reacted with an isocyanate of formula XI:

$R_{10}N=C=O$ (XI), wherein $R_{10}$ is as defined hereinbefore except that $R_{10}$ is not hydrogen, the reaction being optionally catalysed by a base and carried out in an inert reaction medium, ($R_{11}$=hydrogen in the compound of formula IIa), or b) reacted at reflux temperature with a carbonate of formula XIV:

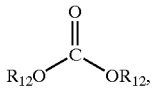
(XIV)

wherein $R_{12}$ is $C_1$–$C_6$alkyl, $C_1$–$C_6$haloalkyl, $C_3$–$C_6$alkenyl or benzyl, wherein the phenyl ring of the benzyl group may be substituted by $C_1$–$C_4$alkyl, halogen, $C_1$–$C_4$haloalkyl, $C_1$–$C_4$alkoxy or by nitro, and the compound of formula IIb:

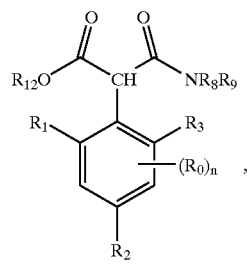
(IIb)

wherein $R_0$, $R_1$, $R_2$, $R_3$, $R_8$, $R_9$, $R_{12}$ and n are as defined hereinbefore, is obtained initially and that compound is then reacted in an inert solvent with an amine of formula X:

 (X), wherein $R_{10}$ and $R_{11}$ are as defined hereinbefore, or
2) a phenylacetic acid ester of formula VIII:

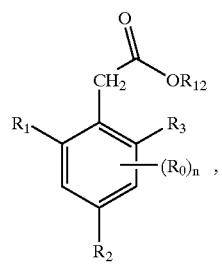
(VIII)

wherein $R_0$, $R_1$, $R_2$, $R_3$, $R_{12}$ and n are as defined hereinbefore, is either
c) reacted with an isocyanate of formula XV:

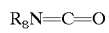 (XV), wherein $R_8$ is as defined hereinbefore except that $R_8$ is not hydrogen, the reaction being optionally catalysed by a base and carried out in an inert reaction medium, and the compound of formula IIb:

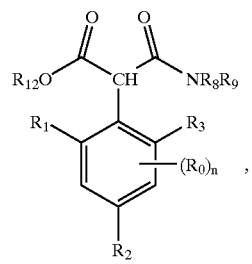
(IIb)

wherein $R_0$, $R_1$, $R_2$, $R_3$, $R_8$, $R_{12}$ and n are as defined hereinbefore and $R_9$ is hydrogen, is obtained initially, and that compound is then reacted in an inert solvent, in the manner described under 1) b), with an amine of formula X, or d) reacted with a carbonate of formula XVI

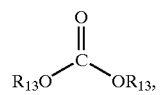
(XVI)

wherein $R_{13}$ has the same meanings as $R_{12}$, at elevated temperature, and a phenylmalonic acid diester of formula III:

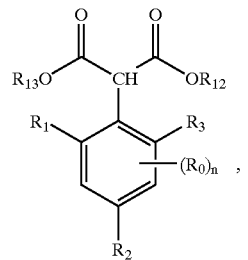
(III)

wherein $R_0$, $R_1$, $R_2$, $R_3$, $R_{12}$, $R_{13}$ and n are as defined hereinbefore, is obtained initially and that compound is then reacted in an inert solvent, in a manner analogous to that described under 1) b), with an amine of formula IX or X:

 (IX) or

 (X), wherein $R_8$, $R_9$, $R_{10}$ and $R_{11}$ are as defined hereinbefore.

The above process variants are illustrated in the following Reaction Scheme 3.

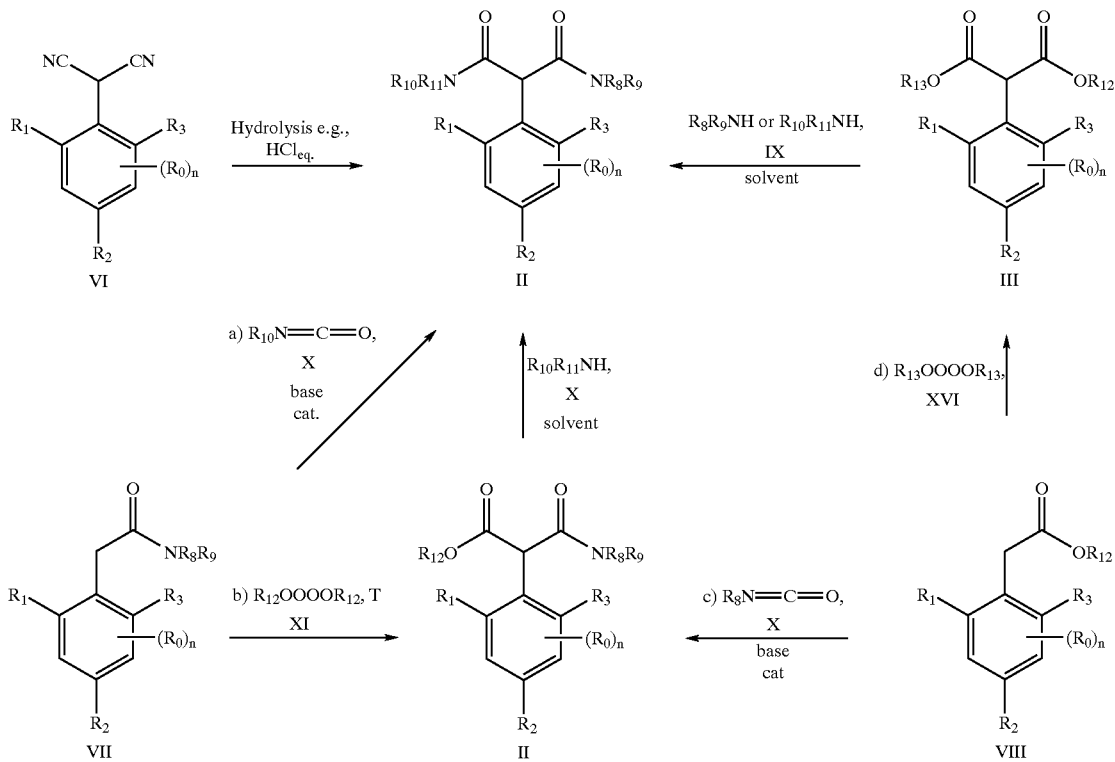

Reaction Scheme 3

The phenylmalonic acid diamides of formula IIa can be obtained in accordance with Reaction Scheme 3 (variant a)), according to known standard procedures, from phenyl acetamides of formula VII using the isocyanates of formula XI, the reaction being optionally catalysed by a base and carried out in an inert solvent.

According to Reaction Scheme 3 (variant b)), the phenylmalonic acid diamides of formula IIa can be obtained from the phenyl acetamides of formula VVI also by heating for several hours at reflux temperature in carbonates of formula XIV as solvents, via compounds of formula IIb and with subsequent amidation in a solvent using amines of formula X. Analogous reactions with phenylacetic acid ester derivatives and carbonates of formula XVI are described, for example, in WO 97/02243.

Further alternative processes for the preparation of the phenylmalonic acid diamides of formula IIa, which start from the phenylacetic acid esters of formula VIII, are provided according to Reaction Scheme 3 by the following two process variants: according to variant c), the compounds of formula VIII can, for example, first of all be reacted analogously to Tetrahedron Lett. 1974, 2427 with isocyanates of formula XV, the reaction being catalysed by a base and carried out in an inert reaction medium, to form the compounds of formula IIb ($R_9$=hydrogen), which are then amidated in an inert solvent in a manner analogous to variant b) using amines of formula X; or, according to variant d), the compounds of formula VIII can, for example, first of all be reacted at reflux temperature, in carbonates of formula XVI as solvents, to form the phenylmalonic acid diesters of formula II, which are then amidated in a solvent in a manner analogous to variant b) using amines of formula IX or X.

The compounds of formulae IV, IVa and IVb are either known or can be prepared analogously to known procedures.

Processes for the preparation of compounds of formula IV are described, for example, in WO 95/00521 and PCT/EP Application number 99/01593.

The phenylmalonic acid dinitrile derivatives of formula VI are either known or can be prepared analogously to known procedures as described, for example, in Chem. Commun. 1984, 932 or J. Am. Chem. Soc. 121, 1473 (1999).

The phenyl acetamides and phenylacetic acid esters of formulae VII and VIII are known. Phenylacetic acid esters of formula VIII are described, for example, in WO 97/02243.

The reagents of formulae IX, X, XI, XII and XIIa, XIIb, XIIc, XIId, XIIe and XIIf, XIV, XV and XVI used in Reaction Schemes 1, 2 and 3, respectively, are either known or can be prepared analogously to known procedures.

The present process is distinguished by:
a) easy accessibility of the starting compounds of formula II,
b) simple reaction procedure and working up,
c) generally high product yields,
d) an economically and ecologically advantageous one-pot process for further derivatisation of the compounds of formula I to produce compounds of formula Ia (e.g. conversion of substituent G to $G_0$), and
e) its economic and ecological advantages derived from the fact that the individual process steps, starting from the preparation of the compounds of formula II (Reaction Scheme 3), the reaction thereof with compounds of formula IV, IVa or IVb to form compounds of formula I (Reaction Scheme 1) and the reaction thereof with electrophiles of formula XII, XIIa, XIIb, XIIc or XIId, can be used for a continuous reaction procedure for the preparation of compounds of formula Ia.

The present preparation process is suitable also especially for the large-scale preparation of 4-aryl-5-oxopyrazoline derivatives of formulae I and Ia.

The Examples that follow further illustrate the process according to the invention without limiting it.

PREPARATION EXAMPLES

Example P1

Preparation of 2,4,6-Trimethylphenylmalonic Acid Diamide

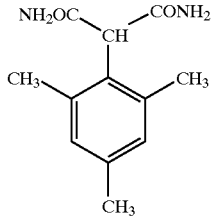

A solution of 2.0 g (0.0109 mol) of 2,4,6-trimethylphenylmalonic acid dinitrile in 5 ml of dichloromethane is added dropwise within a period of 2 minutes to a mixture of 5 ml of concentrated sulfuric acid (97%) and 0.4 ml (0.022 mol) of water. After stirring for 100 hours at 20° C., the reaction mixture is poured onto ice and extracted twice with ethyl acetate. The combined organic phases are washed with saturated sodium chloride solution, dried over sodium sulfate and concentrated in vacuo at 60° C. 2.0 g (83% of theory) of the desired title compound are obtained in the form of yellowish crystals, m.p. 177–179° C.

Example P2

Preparation of 2,6-Diethyl-4-Methylthenylmalonic Acid Diamide

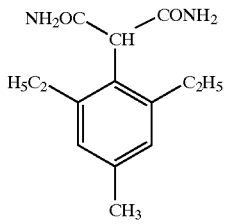

2.1 g (0.0099 mol) of 2,6-diethyl-4-methylphenylmalonic acid dinitrile are added to a mixture of 5 ml of concentrated sulfuric acid (97%) and 0.36 ml (0.0198 mol) of water. After stirring for 5 minutes at 50° C., a homogeneous red-coloured solution forms which is further stirred for 5 hours at 50° C. The reaction mixture is then cooled to 22° C. and subsequently poured into ice-water. After extraction twice with ethyl acetate, the combined organic phases are washed with saturated sodium chloride solution, dried over sodium sulfate and concentrated in vacuo at 60° C. 2.35 g (95.6% of theory) of the desired title compound are obtained in the form of yellowish crystals, m.p. 184–186° C. $^1$H-NMR (CDCl$_3$): 7.19 ppm (broad s, 1H); 6.99 ppm (s, 2H); 5.78 ppm (broad s, 1H); 4.69 ppm (s, 1H); 2.55 ppm (q, 4H); 2.32 ppm (s, 3H 1.21 ppm (t, 6H).

Example P3

Preparation of 8-(2,4,6-Trimethylphenyl) tetrahydropyrazolo [1,2-d][1,4,5]oxadiazepine-7,9-dione

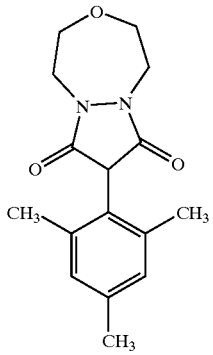

A solution of 1.5 g (0.0068 mol) of 2,4,6-trimethylphenylmalonic acid diamide, 2.16 g (0.0082 mol) of [1,4,5]oxadiazepane dihydrobromide and 2.93 g (0.029 mol) of triethylamine. in 50 ml of xylene is heated for two hours at reflux temperature in a nitrogen atmosphere. The suspension formed is cooled to 22° C., stirred with 1N hydrochloric acid and filtered. The crystalline residue is washed with water and then with diethyl ether and dried in vacuo at 60° C. The desired title compound has a melting point of 248–250° C.

Example P4

Preparation of 8-(2,6-Diethyl-4-methylphenyl) tetrahydropyrazolo[1,2-d][1,4,5]1-oxadiazepine-7,9-dione

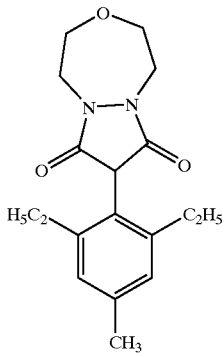

A solution of 2.15 g (0.00866 mol) of 2,6-diethyl-4-methylphenylmalonic acid diamide, 2.64 g (0.010 mol) of [1,4,5]oxadiazepane dihydrobromide and 3.54 g (0.035 mol) of triethylamine in 50 ml of xylene is heated for 2 hours at reflux temperature in a nitrogen atmosphere. The resulting suspension is cooled to 22° C., 50 ml of 1N hydrochloric acid are added and the batch is stirred for 5 minutes. After the addition of 50 ml of hexane, the resulting solid is filtered off, washed with a small amount of water and hexane and dried in vacuo at 80° C. 2.15 g of the desired title compound are obtained in the form of a colourless solid, m.p. 193–194° C. The organic phase is dried over sodium sulfate and concentrated in vacuo at 60° C. to yield a further 0.23 g of the desired title compound. Total yield 2.38 g (87% of theory). $^1$H-NMR (CDCl$_3$): 6.92 ppm (d, 2H); 4.72 ppm (s, 1H); 4.30 ppm (m, 2H); 3.98 (m, 4H); 3.79 ppm (m, 2H); 2.80 ppm (s, 3H); 2.70 ppm (q, 2H); 2.27 ppm (q, 2H); 1.27 ppm (t, 3H); 1.20 ppm (t, 3H).

Example P5

Preparation of 8-(2,6-Diethyl-4-methylPhenyl) tetrahydropyrazolor[1,2-d][1,4,5]-oxadiazepine-7.9-dione

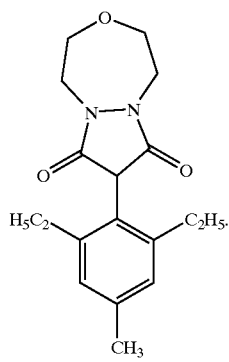

A solution of 0.55 g (0.002 mol) of 2-(2,6-diethyl-4-methylphenyl)-N,N'-dimethylmalonamide, 0.42 g (0.0024 mol) of [1,4,5]oxadiazepane dihydrobromide and 1.17 ml (0.0084 mol) of triethylamine in 6 ml of xylene is heated for 18 hours at reflux temperature in a nitrogen atmosphere. The reaction mixture is then poured into water, the mixture is rendered acidic with 2N hydrochloric acid and the suspension is stirred with hexane. The solid is filtered off, washed with water and hexane and dried in vacuo at 50° C. 0.33 g of the desired title compound is obtained in the form of beige crystals, m.p. 192–193.5° C.

Example P6

One-pot Process for the Preparation of 2,2-Dimethylpropionic acid 8-(2,6-diethyl-4-methylphenyl)-9-oxo-1,2,4,5-tetrahydro-9H-pyrazolor[1,2-d][1,4,5]oxadiazeoin-7-yl ester

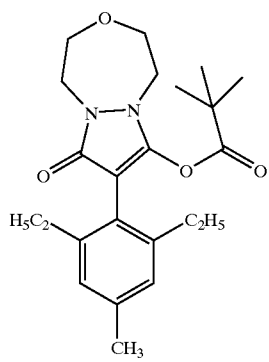

A solution of 1.0 g (0.004 mol) of 2,6-diethyl-4-methylphenylmalonic acid diamide, 0.84 g (0.0048 mol) of [1,4,5]oxadiazepane dihydrobromide and 1.62 g (0.016 mol) of triethylamine in 25 ml of xylene is heated for 2 hours at reflux temperature in a nitrogen atmosphere. The reaction mixture is then cooled to room temperature, 0.87 g (0.0072 mol) of pivaloyl chloride is added and the batch is stirred for a further 2 hours at 22° C. The reaction mixture is then stirred with 25 ml of 1N hydrochloric acid and extracted with ethyl acetate. The organic extracts are washed with saturated sodium chloride solution, dried over sodium sulfate and concentrated in vacuo at 600C. 2.3 g of brown oil are obtained. Recrystallisation from hexane yields 1.0 g of the desired title compound in the form of colourless crystals, m.p. 120–122° C.

$^1$H-NMR (CDCl$_3$): 6.89 ppm (s, 2H); 4.29 ppm (m, 2H); 3.95 ppm (m, 2H); 3.87 ppm (m, 4H); 2.49 ppm (m, 4H); 2.30 ppm (s, 3H); 1.12 ppm (t, 6H); 1.04 ppm (s, 9H).

Example P7

Preparation of 2-(2,6-Diethyl-4-methyylhenyl)-N,N'-dimethylmalonamide

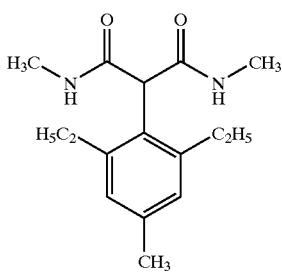

30 ml of a 33% solution of methylamine in ethanol are added to 4.18 g (0.015 mol) of 2-(2,6-diethyl-4-methylphenyl)malonic acid dimethyl ester at 22° C. and the batch is stirred at 75° C. for 30 hours. The reaction mixture is then poured into water, and the mixture is rendered acidic with concentrated hydrochloric acid and extracted with ether. The organic extracts are washed with saturated sodium chloride solution, dried over magnesium sulfate and concentrated in vacuo at 60° C. The residue obtained (4.0 g of a brown oil) is stirred with hexane, 1.74 g of the desired title compound being obtained in the form of a crystalline product, m.p. 98–100° C.

Example P8

Preparation of 2-(2,4,6-TrimethylDhenyl) tetrahydropyrazolor1,2-aloyridazine-1,3-dione (without the addition of a base)

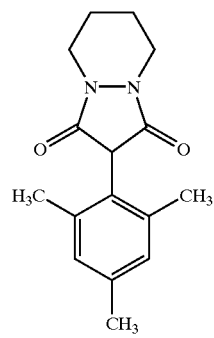

A solution of 2.05 g (0.0093 mol) of 2,4,6-trimethylphenylmalonic acid diamide and 0.95 g (0.0110 mol) of hexahydropyridazine in 50 ml of xylene is boiled for 2 hours at reflux temperature under nitrogen. The reaction mixture is then cooled to 22° C. and stirred with 50 ml of 1N hydrochloric acid; the resulting suspension is filtered and the crystalline residue is washed first with diethyl ether and then with water and dried in vacuo. 2.2 g of the desired title compound are obtained in the form of colourless crystals, m.p. 247–248° C.

$^1$H-NMR (CDCl$_3$): 6.93 ppm (s, 1H); 6.83 ppm (s, 1H); 4.65 ppm (s, 1H); 3.67 ppm (broad s, 4H); 2.40 ppm (s, 3H); 2.27 ppm (s, 3H); 2.04 ppm (s, 3H); 1.83 ppm (broad s, 4H).

Example P9

Preparation of 2,6-Diethyl-4-(4-pyridyl) phenylmalonic Acid Diamide

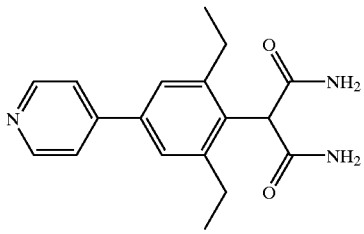

36 mg (0.002 mol) of water and then 360 mg (about 75%, 0.001 mol) of (2,6-diethyl-4-(4-pyridyl)phenylmalonic acid dinitrile are added to 0.5 ml of sulfuric acid (97%) and the batch is stirred at 50° C. for 5.5 hours. The cooled reaction mixture is neutralised with saturated sodium hydrogen carbonate solution, the resulting precipitate is filtered off and washed with water, and the crystals are suspended with a small amount of diethyl ether, filtered off and dried. The desired title compound is obtained in a yield of 145 mg (47% of theory), m.p. 184–186° C.

$^1$H-NMR (CDCl$_3$): 8.63 ppm (d, 2H); 7.48 ppm (d, 2H); 7.40 ppm (s, 2H); 7.20 ppm (broad signal, 2H); 5.81 ppm (broad signal, 2H); 4.80 ppm (s, 1H); 2.68 ppm (q, 4H); 1.30 ppm (t, 6H).

The following compound (Example P10) is also obtained analogously to the above Example: 2,6-diethyl-4-(2-pyridyl) phenylmalonic acid diamide, m.p. 230° C. (decomposition) and $^1$H-NMR (CDCl$_3$): 8.68 ppm (d, 1H); 4.66–7.80 ppm (m, 4H); 7.23 ppm (m, 1H); 7.20 ppm (broad signal, 2H); 5.67 ppm (broad signal, 2H); 4.80 ppm (s, 1H); 2.67 ppm (q, 4H); 1.30 ppm (t, 6H).

Example P11

Preparation of 2,2-Dimethylpropionic acid 8-(2.6-diethyl-2-pyridin-4-ylphenyl)-9-oxo-1,2,4,5-tetrahydro-9H-pyrazolo[1,2-d][1,4,5]oxadiazepin-7-yl Ester

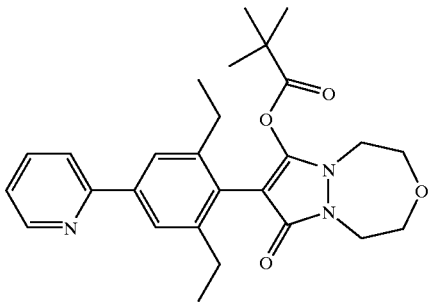

290 mg (0.0011 mol) of [1,4,5]oxadiazepane dihydrobromide and 0.56 ml (0.004 mol) of triethylamine are introduced into 7 ml of degassed xylene, 311 mg (0.001 mol) of 2,6-diethyl-4-(2-pyridyl)phenylmalonic acid diamide are added, and the batch is stirred at 150° C. for 4 hours. The reaction mixture is left to stand overnight at 20° C., is then cooled to from 0 to 5° C. and 0.135 ml (0.0011 mol) of pivalic acid chloride is added dropwise. The batch is stirred for 3 hours at 20° C. to complete the reaction, poured into ice-water and extracted twice with ethyl acetate. The combined organic phases are washed with water and brine, dried over sodium sulfate and concentrated. The crude product of 345 mg (75% of theory) is crystallised from diethyl ether. The desired title compound is obtained in a yield of 160 mg (35% of theory), m.p. 146–147° C.

$^1$H-NMR (CDCl$_3$): 8.70 ppm (m, 1H); 7.72 ppm (m, 2H); 7.70 ppm (s, 2H); 7.22 ppm (m, 1H); 4.30 ppm (m, 2H); 3.97 ppm (m, 2H); 3.89 ppm (m, 4H); 2.62 ppm (m, 4H); 1.21 ppm (t, 6H); 1.03 ppm (s, 9H).

The following compound (Example P12) is also obtained analogously to the above Example: 2,2-dimethylpropionic acid 8-(2,6-diethyl-4-pyridin-4-ylphenyl)-9-oxo-1,2,4,5-tetrahydro-9.H.-pyrazolo[1,2-d][1,4,5]oxadiaze in-7-yl ester, $^1$H-NMR (CDCl$_3$): 8.19 ppm (broad signal, 2H); 7.53 ppm (broad signal, 2H); 7.35 ppm (s, 2H); 4.30 ppm (m, 2H); 3.96 ppm (m, 2H); 3.89 ppm (m, 4H); 2.62 ppm (m, 4H); 1.20 ppm (t, 6H); 1.05 ppm (s, 9H).

What is claimed is:

1. A process for the preparation of a compound of formula I:

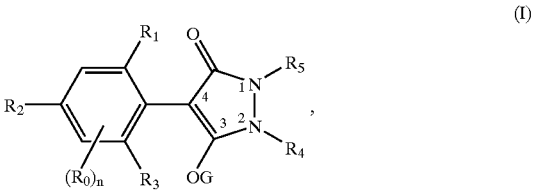

wherein

R$_0$ is, each independently of any other, halogen, C$_1$–C$_6$alkyl, C$_2$–C$_6$alkenyl, C$_2$–C,alkynyl, C$_1$–C$_6$haloalkyl, cyano-C$_1$–C$_6$alkyl, C$_2$–C$_6$haloalkenyl, cyano-C$_2$–C$_6$alkenyl, C$_2$–C$_6$haloalkynyl C$_2$–C$_6$alkynyl, hydroxy, hydroxy-C$_1$–C$_6$alkyl, C$_1$–C$_6$alkoxy, nitro, amino, $C_1$–$C_6$alkylamino, di($C_1$–$C_6$alkyl)amino, $C_1$–$C_6$alkylcarbonylamino, $C_1$–$C_6$alkylsulfonylamino, $C_1$–$C_6$alkylaminosulfonyl, $C_1$–$C_6$alkylcarbonyl, $C_1$–$C_6$alkylcarbonyl-$C_1$–$C_6$alkyl, $C_1$–$C_6$alkoxycarbbnyl-$C_1$–$C_6$alkyl, $C_1$–$C_6$alkylcarbonyl-$C_2$–$C_6$alkenyl, $C_1$–$C_6$alkoxycarbonyl-$C_2$–$C_6$alkenyl, $C_1$–$C_6$alkylcarbonyl-$C_2$–$C_6$alky $C_1$–$C_6$alkoxycarbonyl-$C_2$–$C_6$alkynyl, $C_1$–$C_6$alkoxycarbonyl, cyano, carboxyl, phenyl or an aromatic ring that contains 1 or 2 hetero atoms selected from the group consisting of nitrogen oxygen and sulfur, wherein the latter two aromatic rings may be substituted by $C_1$–$C_3$alkyl, $C_1$–$C_3$haloalkyl, $C_1$–$C_3$alkoxy, $C_1$–$C_3$haloalkoxy, halogen, cyano or by nitro;

$R_1$, $R_2$ and $R_3$ are each independently of the others $C_1$–$C_6$alkyl, n is 0;

$R_4$ and $R_5$ together with the nitrogen atoms to which they are bonded form a saturated 5- to 8-membered ring which is interrupted by oxygen; and G is hydrogen, which process comprises reacting a compound of formula II:

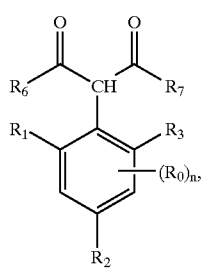

(II)

wherein $R_0$, $R_1$, $R_2$, $R_3$ and n are as defined hereinbefore; $R_6$ is $R_8R_9N$—; $R_7$ is $R_{10}R_{11}N$— or $R_{12}O$—; and $R_8$, $R_9$, $R_{10}$, $R_{11}$ and $R_{12}$ are each independently of the others hydrogen, $C_1$–$C_6$alkyl, $C_1$–$C_6$haloalkyl, $C_3$–$C_6$alkenyl or benzyl, wherein the phenyl ring of the benzyl group may be substituted by $C_1$–$C_4$alkyl, halogen, $C_1$–$C_4$haloalkyl, $C_1$–$C_4$alkoxy or by nitro, in an inert organic solvent, optionally in the presence of a base, with a compound of formula IV, IVa or IVb:

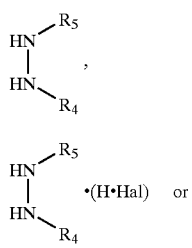

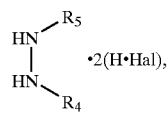

wherein $R_4$ and $R_5$ are as defined hereinbefore and H.Hal is a hydrogen halide, and optionally converting the resulting compound of formula I wherein G is a metal ion equivalent or an ammonium cation, by salt conversion into the corresponding salt of formula I wherein G is a sulfonium or phosphonium cation, or by treatment with a Brönsted acid into the corresponding compound of formula I wherein G is hydrogen.

2. A process according to claim 1, wherein $R_1$, $R_2$ and $R_3$ are each independently of the others $C_1$–$C_4$alkyl.

3. A process according to claim 1, which comprises using a compound of formula II wherein $R_8$, $R_9$, $R_{10}$, $R_{11}$ and $R_{12}$ are hydrogen, $C_1$–$C_6$alkyl or benzyl.

4. A process according to claim 1, wherein the compound of formula IV, IVa or IVb is used in an equimolar amount or in an excess of from 5 to 50 mol %, based on the compound of formula II.

5. A process according to claim 1, wherein the reaction is carried out at a reaction temperature of from 0° to 200° C.

6. A process according to claim 1, which comprises using as the inert organic solvent for the reaction an aromatic, aliphatic or cycloaliphatic hydrocarbon, halogenated hydrocarbon, an ether, nitrile, dialkyl sulfoxide, amide or lactam, an alcohol, glycol or polyalcohol, a carboxylic acid, or a mixture of such solvents.

7. A process according to claim 6, which comprises using as the solvent toluene, one of the xylene isomers ortho-, meta- and para-xylene, methylcyclohexane, chlorobenzene or one of the dichlorobenzene isomers 1,2-, 1,3- and 1,4-dichlorobenzene.

8. A process according to claim 1, which comprises carrying out the reaction in an inert gas atmosphere.

9. A process according to claim 1, which comprises carrying out the reaction of a compound of formula II with a compound of formula IV with or without the addition of a base.

10. A process according to claim 1, which comprises carrying out the reaction of a compound of formula II with a compound of formula IVa or IVb in the presence of a base.

11. A process according to claim 10, which comprises using as base a tertiary amine, pyridine, alkali metal alcoholate, or alkali metal or alkaline earth metal hydride, hydroxide, carbonate or hydrogen carbonate.

12. A process according to claim 11, which comprises using the base in catalytic amounts or in a molar excess of up to 5, based on the compound of formula II.

* * * * *